(12) United States Patent
Zarinetchi et al.

(10) Patent No.: US 7,155,291 B2
(45) Date of Patent: *Dec. 26, 2006

(54) METHODS AND APPARATUS FOR PROVIDING A SUFFICIENTLY STABLE POWER TO A LOAD IN AN ENERGY TRANSFER SYSTEM

(75) Inventors: Farhad Zarinetchi, Chelmsford, MA (US); Stephen J. Keville, Harvard, MA (US)

(73) Assignee: Abiomed, Inc., Danvers, MA (US)

( * ) Notice: Subject to any disclaimer, the term of this patent is extended or adjusted under 35 U.S.C. 154(b) by 792 days.

This patent is subject to a terminal disclaimer.

(21) Appl. No.: 10/136,089

(22) Filed: May 1, 2002

(65) Prior Publication Data

US 2002/0123779 A1 Sep. 5, 2002

Related U.S. Application Data

(63) Continuation of application No. 09/635,050, filed on Aug. 9, 2000, now Pat. No. 6,442,434.

(60) Provisional application No. 60/223,787, filed on Aug. 8, 2000, provisional application No. 60/160,343, filed on Oct. 19, 1999.

(51) Int. Cl.
*A61N 1/08* (2006.01)

(52) U.S. Cl. ........................... 607/61; 323/911

(58) Field of Classification Search .............. 128/899, 128/903; 302/107, 108; 323/264, 347, 911; 607/2, 17, 32, 33, 61, 62
See application file for complete search history.

(56) References Cited

U.S. PATENT DOCUMENTS

| 3,195,540 A | 7/1965 | Waller |
| 3,756,246 A | 9/1973 | Thaler et al. |
| 4,441,210 A | 4/1984 | Hochmair et al. |
| 4,665,896 A | 5/1987 | LaForge et al. |
| 4,924,171 A | 5/1990 | Baba et al. |

(Continued)

OTHER PUBLICATIONS

N. de N. Donaldson, "Use of Feedback with Voltage Regulators for Implants Powered by Coupled Coils," *Medical and Biological Engineering and Computing*, GB, Peter Peregrinus Ltd. Stevenage, vol. 23, No. 3, May 1, 1985, p. 29, XP002066875, ISSN: 0140-0118.

*Primary Examiner*—Robert E Pezzuto
*Assistant Examiner*—Frances P. Oropeza
(74) *Attorney, Agent, or Firm*—Nutter, McClennen & Fish, LLP

(57) ABSTRACT

Methods and apparatus for providing a sufficiently stable power to a load in an energy transfer system that transfers energy from one side of a physical boundary to another side of the boundary. In one example, a power supply and a primary winding are located on a first side of a physical boundary (e.g., external to a body), and a secondary winding and the load are located on a second side of the physical boundary (e.g., internal to the body). A primary voltage across the primary winding is regulated so as to provide a sufficiently stable output power to the load notwithstanding changes in the load and/or changes in a relative position of the primary winding and the secondary winding. One aspect of the invention relates to energy transfer methods and apparatus for use in connection with the human body. In particular, one example of the invention includes a transcutaneous energy transfer (TET) system for transferring power from a power supply external to the body to a device implanted in the body.

29 Claims, 24 Drawing Sheets

U.S. PATENT DOCUMENTS

| | | |
|---|---|---|
| 4,925,443 A | 5/1990 | Heilman et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,713,939 A | 2/1998 | Nedungadi et al. |
| 5,735,887 A | 4/1998 | Barreras, Sr. et al. |
| 5,741,316 A | 4/1998 | Chen et al. |
| 5,755,748 A | 5/1998 | Borza |
| 5,991,665 A | 11/1999 | Wang et al. |
| 5,995,874 A * | 11/1999 | Borza .......... 607/61 |
| 6,149,683 A | 11/2000 | Lancisi et al. |

* cited by examiner

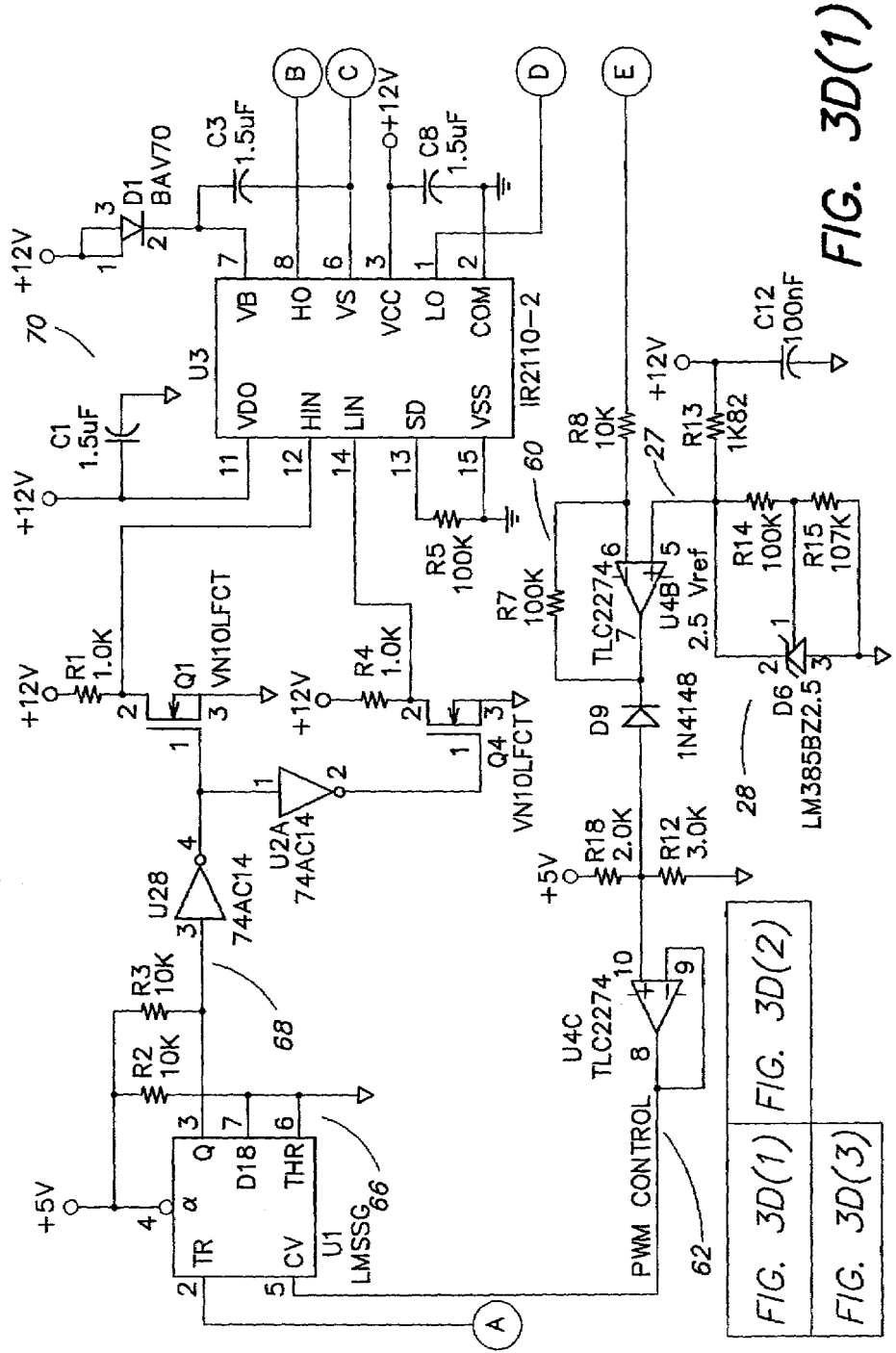
FIG. 3D(1)

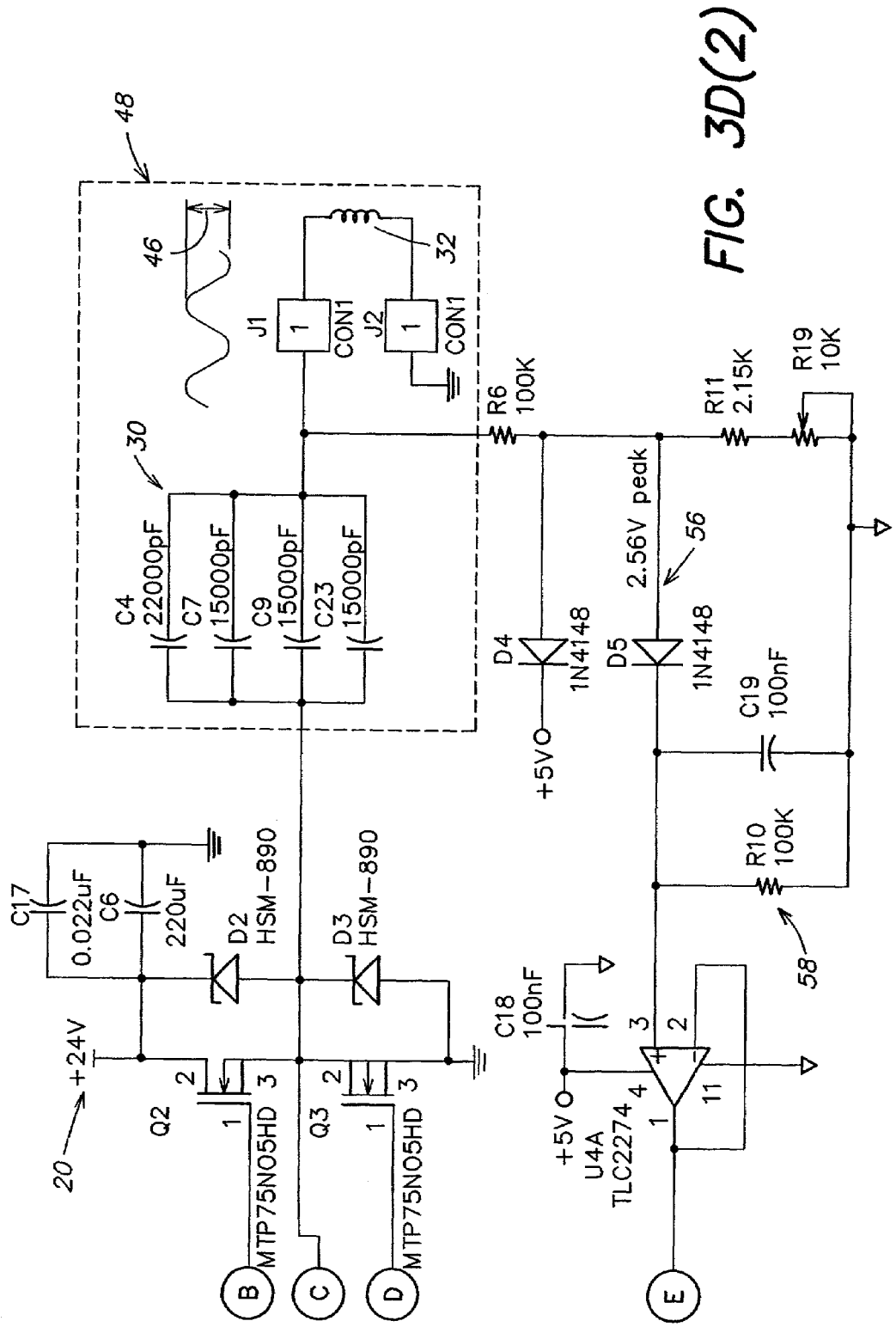
FIG. 3D(2)

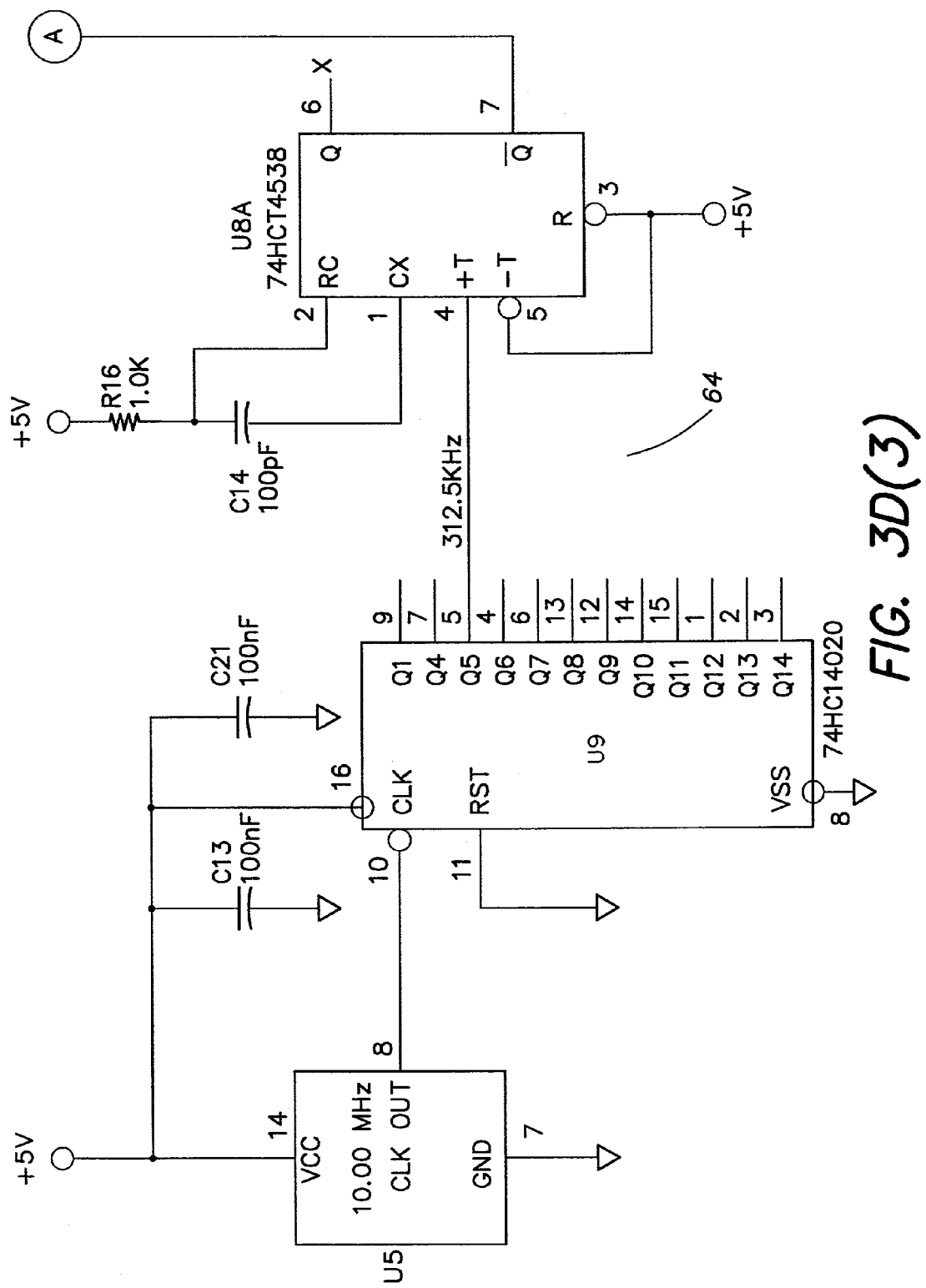
FIG. 3D(3)

METHODS AND APPARATUS FOR PROVIDING A SUFFICIENTLY STABLE POWER TO A LOAD IN AN ENERGY TRANSFER SYSTEM

CROSS REFERENCE TO RELATED APPLICATION

This application is a continuation application of U.S. patent application Ser. No. 09/635,050 filed Aug. 9, 2000 entitled "METHODS AND APPARATUS FOR PROVIDING A SUFFICIENTLY STABLE POWER TO A LOAD IN AN ENERGY TRANSFER SYSTEM," and naming as inventors Farhad Zarinetchi and Stephen J. Keville, now U.S. Pat. No. 6,442,434, which application claims the benefit, under 35 U.S.C. § 119(e), of U.S. Provisional Application Ser. No. 60/160,343, filed Oct. 19, 1999, entitled "ADAPTIVE TET SYSTEM," which application is hereby incorporated by reference and U.S. Provisional Application Ser. No. 60/223,787, filed Aug. 8, 2000, entitled "ADAPTIVE TET SYSTEM," both of which are hereby incorporated by reference.

BACKGROUND OF THE INVENTION

1. Field of the Invention

The present invention relates to energy transfer methods and apparatus. More particularly, the invention relates to providing a sufficiently stable power to a load in an energy transfer system that transfers power across a physical boundary (e.g., from a power supply located external to a body to a load located internal to the body).

2. Related Art

In a variety of scientific, industrial, and medically related applications, it may be desirable to transfer energy or power (energy per unit time) across some type of boundary. For example, one or more devices that require power (e.g., electrical, mechanical, optical, and acoustic devices) may be located within the confines of a closed system, or "body," in which it may be difficult and/or undesirable to also include a substantial and/or long term source of power. The closed system or body may be delimited by various types of physical boundaries, and the system internal to the boundary may be living or inanimate, may perform a variety of functions, and may have a variety of operational and physical requirements and/or constraints. In some cases, such requirements and constraints may make the implementation of a substantial and/or long term "internal" power source for internally located devices problematic.

In some closed systems, repeated entry into the system may be undesirable for a variety of reasons. In other closed systems, significant internal power requirements and a limited internal space may prohibit the implementation of a suitably sized internal power source. In yet other systems, contamination and/or security issues may pose particular challenges in implementing an internal power source. For any combination of the foregoing and other reasons, a power source external to the system and some feasible means of transferring power from the external source to one or more internal devices may be preferable in some applications.

One example of a closed system is the human body. In some medically related and scientific applications, a variety of prosthetic and other devices that require power may be surgically implanted within various portions of the body. Some examples of such devices include a synthetic replacement heart, a circulatory blood pump or ventricular assist device (VAD), a cochlear (ear) implant, a pacemaker, and the like. With respect to the human body, issues such as repeated reentry or surgery, internal space limitations, and contamination (e.g., infection) may make the implementation of a suitable internal power source for some of these implanted devices impractical.

Accordingly, in some medical implant applications, "transcutaneous energy transfer" (TET) devices are employed to transfer energy from outside the body to inside the body, to provide power to one or more implanted prostheses or devices from an external power source. One example of a conventional TET device is a transformer that includes a primary winding (or coil) external to the body and a secondary winding internal to the body. Both the primary and secondary windings generally are placed proximate to respective outer and inner layers of a patient's skin; hence, the term "transcutaneous" commonly refers to energy transfer "through the skin." Energy is transferred from the primary winding to the secondary winding in the form of a magnetic field. The implanted secondary winding converts the transferred energy in the magnetic field to electrical power for the implanted device, which acts as a "load" on the secondary winding.

In general, TET devices differ from conventional power transformers in that power transformers typically include a magnetic core around which the primary and secondary windings are wound, thus fixing the relative positions of the primary and secondary windings. In contrast, the primary and secondary windings of conventional TET devices are not necessarily fixed in position with respect to one another. Accordingly, one issue associated with conventional TET devices is that the power supplied by the secondary winding to a load (e.g., an implanted device) may be quite sensitive to more than nominal or trivial physical displacements of either the primary winding or the secondary winding from an optimum coupling position. The resolution of this issue determines the suitability of the TET technology to a particular type of load.

For example, implanted prostheses or other devices, and particularly an implanted device that performs a life sustaining function, generally must have a consistent source of available power. Without a consistent power source, the implanted device may function erratically or intermittently. Such an erratic or intermittent operation can have undesirable, and in some cases serious life threatening effects on the patient. Accordingly, with TET devices in particular, and other energy transfer systems in general which transfer energy across a boundary, it is desirable to accurately and reliably provide a sufficiently stable power to the load.

SUMMARY OF THE INVENTION

One embodiment of the invention is directed to an apparatus for use in a transcutaneous energy transfer system that includes a power supply, a primary winding and a secondary winding. The apparatus comprises a control circuit, coupled to the power supply and the primary winding, to monitor a primary amplitude of a primary voltage across the primary winding and to control the primary amplitude based only on the monitored primary amplitude and a reference voltage.

Another embodiment of the invention is directed to a method in a transcutaneous energy transfer system including a power supply, a primary winding and a secondary winding. The method comprises acts of monitoring a primary amplitude of a primary voltage across the primary winding, and regulating the primary amplitude based only on the monitored primary amplitude and a reference voltage.

Another embodiment of the invention is directed to an energy transfer system for transferring power from a power supply located on a first side of a physical boundary to a variable load located on a second side of the physical boundary. The energy transfer system comprises a primary winding electrically coupled to the power supply to generate a magnetic field based on input power provided by the power supply, wherein the magnetic field permeates the physical boundary. The system also comprises a secondary winding, magnetically coupled to the primary winding via the magnetic field, to receive at least a portion of the magnetic field. The secondary winding is electrically coupled to the variable load to provide output power to the variable load based on the received magnetic field. The system also comprises at least one control circuit, electrically coupled to at least the primary winding, to regulate a primary voltage across the primary winding such that a sufficiently stable output power is provided to the variable load notwithstanding at least one of changes in the load and changes in a relative position of the primary winding and the secondary winding.

Another embodiment of the invention is directed to a method of transferring power from a power supply to a variable load in an energy transfer system that includes a primary winding electrically coupled to the power supply located on a first side of a physical boundary, and a secondary winding electrically coupled to the variable load located on a second side of the physical boundary. The method comprises an act of regulating a primary voltage across the primary winding so as to provide a sufficiently stable output power to the variable load notwithstanding at least one of changes in the variable load and changes in a relative position of the primary winding and the secondary winding.

Another embodiment of the invention is directed to an apparatus for use in an energy transfer system, wherein the energy transfer system includes a power supply electrically coupled to a primary winding, and a secondary winding magnetically coupled to the primary winding. The primary and secondary windings are used to transfer power from the power supply to a load that is electrically coupled to the secondary winding. The primary winding and the secondary winding do not have a fixed spatial relationship to each other. The apparatus comprises a secondary circuit, electrically coupled to the secondary winding, to monitor a measurable quantity associated with the load and to provide a detectable indication based on the monitored measurable quantity. The apparatus also comprises a primary circuit, electrically coupled to the primary winding, to monitor the detectable indication provided by the secondary circuit and to regulate a primary voltage across the primary winding based on the detectable indication so as to regulate a load voltage across the load.

Another embodiment of the invention is directed to a method in a transcutaneous energy transfer system that includes a power supply electrically coupled to a primary winding and a secondary winding magnetically coupled to the primary winding. The primary and secondary windings are for transferring power from the power supply to a load that is electrically coupled to the secondary winding. The primary winding and the secondary winding do not have a fixed spatial relationship to each other. The method comprises acts of making a comparison of a measurable quantity associated with the load and a predetermined threshold level, activating a secondary circuit to provide a detectable indication based on the comparison, and regulating a primary voltage across the primary winding based on the detectable indication.

Another embodiment of the invention is directed to an energy transfer system for transferring power from a power supply located on a first side of a physical boundary to a variable load located on a second side of the physical boundary. The energy transfer system comprises a primary winding electrically coupled to the power supply to generate a magnetic field based on input power provided by the power supply, and a secondary winding magnetically coupled to the primary winding to receive at least a portion of the magnetic field generated by the primary winding. The secondary winding provides output power to the variable load based on the received magnetic field, and the magnetic field forms a portion of a power channel between the primary winding and the secondary winding to transfer at least some of the power from the power supply to the variable load. The energy transfer system also comprises a first control circuit, electrically coupled to the primary winding, to regulate a load voltage across the variable load based on information related to the variable load that is obtained via the power channel.

Another embodiment of the invention is directed to a method in an energy transfer system for transferring power from a power supply located on a first side of a physical boundary to a variable load located on a second side of the physical boundary. The energy transfer system includes a primary winding electrically coupled to the power supply to generate a magnetic field based on input power provided by the power supply, and a secondary winding magnetically coupled to the primary winding to receive at least a portion of the magnetic field generated by the primary winding. The secondary winding provides output power to the variable load based on the received magnetic field, and the magnetic field forms a portion of a power channel between the primary winding and the secondary winding to transfer at least some of the power from the power supply to the variable load. The method comprises acts of monitoring the power channel to obtain information related to the variable load, and regulating a load voltage across the variable load based on the information obtained via the power channel.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

FIG. 3D, FIGS. 3D(1), 3D(2), 3D(3), collectively, is a circuit diagram showing one example of an electronic circuit implementation for a primary side of the energy transfer system of FIG. 2, according to one embodiment of the invention;

FIG. 9, FIGS. 9A and 9B, collectively, is a circuit diagram showing one example of an electronic circuit implementation for a secondary side of the energy transfer systems of FIGS. 2 or 5, according to one embodiment of the invention;

FIG. 10, FIGS. 10A–10D, collectively, is a circuit diagram showing one example of an electronic circuit implementation of both primary and secondary sides of the energy transfer system shown in FIG. 5, according to one embodiment of the invention; and FIG. 11, FIGS. 11A–11D, collectively, is a circuit diagram showing another example of an electronic circuit implementation of the primary side of the energy transfer system of FIG. 5, according to one embodiment of the invention.

DETAILED DESCRIPTION

One embodiment of the present invention is directed to methods and apparatus for providing a sufficiently stable power to a load in an energy transfer system. In one aspect of this embodiment, the energy transfer system may transfer energy across a physical boundary. The boundary may be formed, for example, by some inanimate material or living tissue and may be in a solid, liquid or gaseous phase. The boundary may also be formed by a combination of inanimate materials or living tissue in various phases. In another aspect, the boundary may be arranged to form a closed system (e.g., the boundary may completely surround a "body"), and the energy transfer system may be implemented so as to transfer energy, from a position external to the body, across the boundary to a position internal to the body. The transferred energy may be used to provide power to one or more devices located internal to the body. One example of an application of such an energy transfer system is providing power to one or more devices implanted in a human body, as discussed further below.

Figure 1:
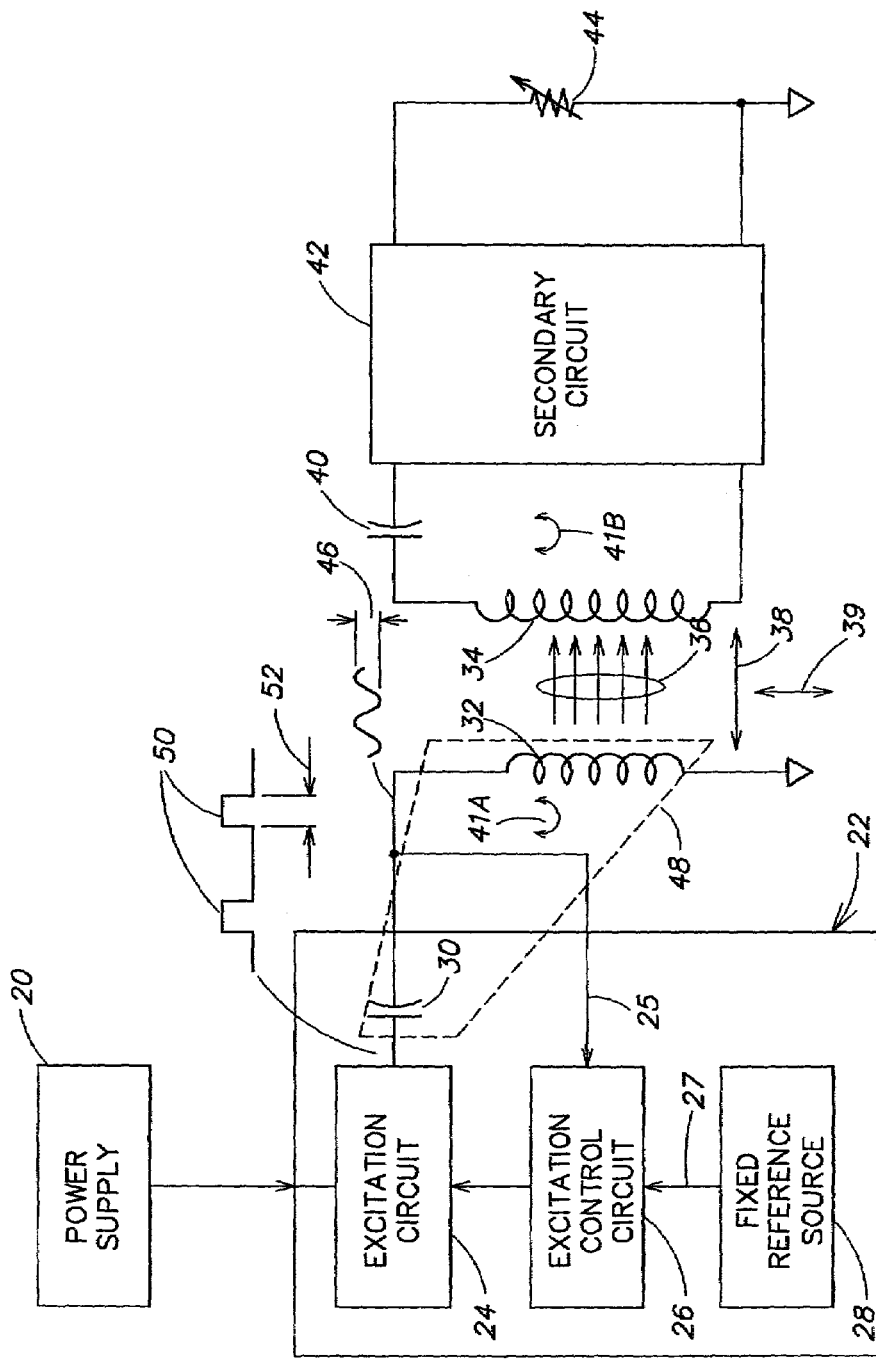
FIG. 1 is a block diagram showing an example of an energy transfer system according to one embodiment of the invention.

As shown in FIG. 1, energy transfer systems according to various embodiments of the invention typically include a power supply 20 and a primary winding 32 electrically coupled to the power supply to generate a magnetic field 36 based on input power provided by the power supply. Energy transfer systems according to the invention also typically include a secondary winding 34 that is magnetically coupled to the primary winding 32 via the magnetic field 36. In FIG. 1, the magnetic field 36 is symbolically illustrated as a number of arrows emanating from the primary winding 32 and propagating toward the secondary winding 34.

According to one embodiment, the primary winding 32 and the secondary winding 34 shown in FIG. 1 are positioned relative to each other such that the secondary winding 34 receives at least a portion of the magnetic field 36. The secondary winding 34 is electrically coupled to a load 44 and provides output power to the load 44 based on the received magnetic field. In various embodiments, the load 44 may represent one or more of a variety of devices that use the output power provided by the secondary winding 34 to perform some function. The load generally is associated with some resistance or impedance that, in some applications, may vary from time to time during normal operation of the load depending, in part, on the particular function that the load is performing. In this manner, the load may be a variable load (as shown symbolically in FIG. 1, for example, by a variable resistor).

According to one embodiment of the invention, the power supply 20 and the primary winding 32 shown in FIG. 1 are located on a first side of a physical boundary (e.g., external to a body), and the secondary winding 34 and the load 44 are located on a second side of the physical boundary (e.g., internal to the body). As discussed above, some energy transfer systems that transfer energy across a boundary (e.g., TET systems) include primary and secondary windings that are not necessarily physically coupled to each other in a rigidly fixed manner (i.e., some movement of the windings relative to each other is possible). Accordingly, these energy transfer systems may be susceptible to output power fluctuations due not only to changes in the load from time to time (i.e., varying load resistance or impedance), but also due to changes in relative position of the primary and secondary windings. For purposes of the present disclosure, the terms "changes in relative position" refer to one or more of an axial displacement between the primary and secondary windings (as indicated, for example, by the reference character 38 in FIG. 1), a lateral displacement between the windings in a direction essentially orthogonal to the axial displacement 38 (as indicated, for example, by the reference character 39 in FIG. 1), and any change in orientation of one winding (e.g., rotation of a winding about an axis of rotation) relative to the other winding (as indicated, for example, by the reference characters 41A and 41B in FIG. 1).

In view of the foregoing, in one aspect of the invention, the energy transfer system is controlled so as to provide a sufficiently stable power to the load notwithstanding one or both of changes in the load from time to time (i.e., varying load resistance or impedance), and changes in relative position of the primary and secondary windings. In particular, in some embodiments, the power ultimately provided to the load may be controlled by regulating various voltages in the system.

Figure 2:
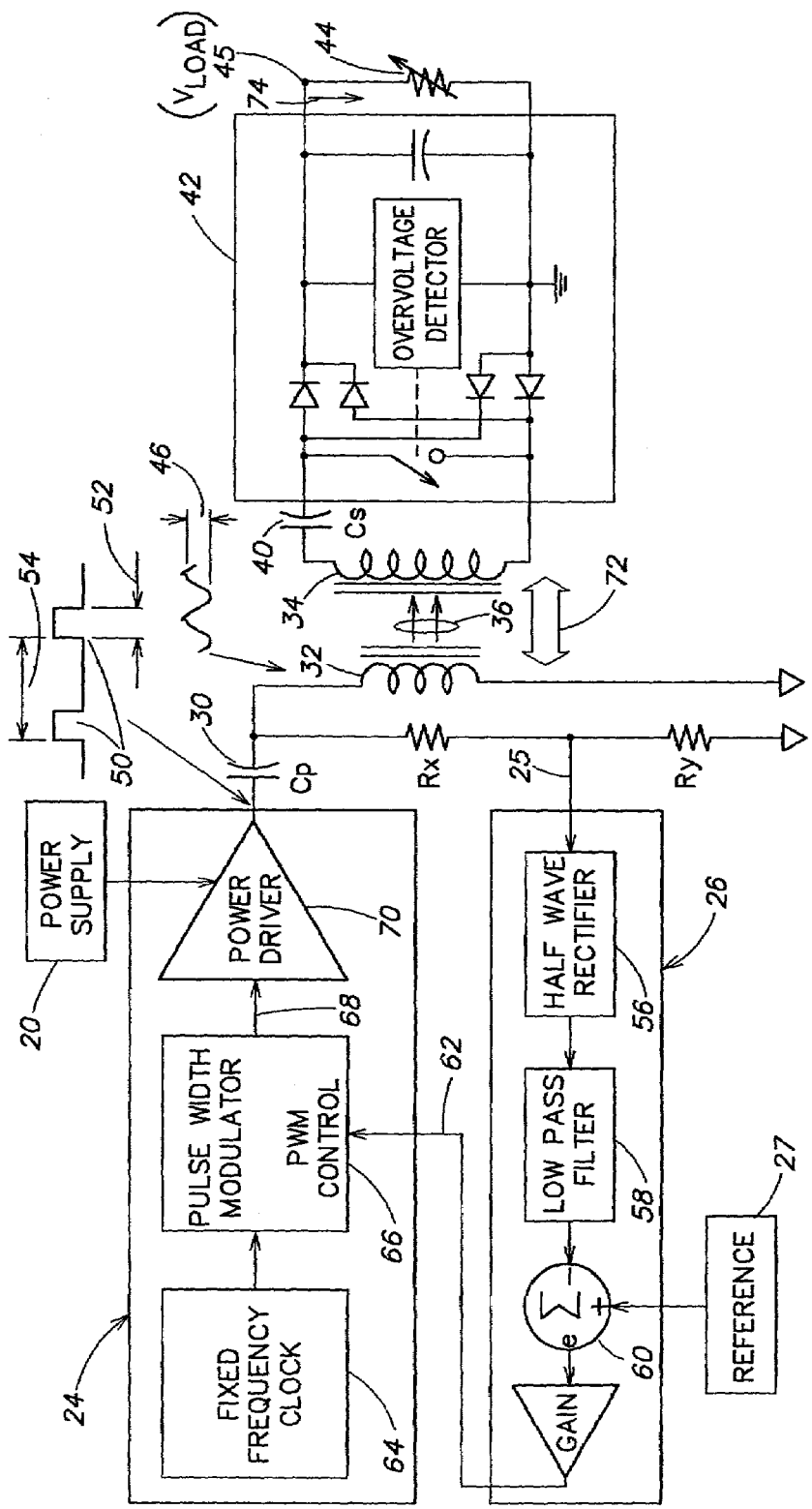
FIG. 2 is a more detailed block diagram of the energy transfer system shown in FIG. 1, according to one embodiment of the invention.

For example, in one illustrative embodiment, as shown in FIGS. 1 and 2 and discussed in greater detail below, a primary amplitude of a primary voltage across the primary winding 32 of the energy transfer system is regulated such that the primary amplitude is held essentially at some constant value that is proportional to a fixed reference parameter (e.g., a reference voltage). In this embodiment, the primary amplitude is regulated essentially independently of system conditions associated with the secondary winding 34 and any circuitry coupled to the secondary winding (including the load). In particular, in one aspect of this embodiment, regulation of the primary amplitude does not necessarily depend upon changes in the load and changes in relative position of the windings. Instead, by selecting an appropriate reference parameter, the primary amplitude is regulated at essentially a constant value such that a sufficiently stable power is provided to the load over a predetermined range for the load voltage, which voltage may nominally fluctuate due to changes in the load and/or changes in relative winding position. At least one favorable feature of this embodiment is simplicity of implementation while nonetheless providing sufficient control of the energy transfer system.

Figure 4:
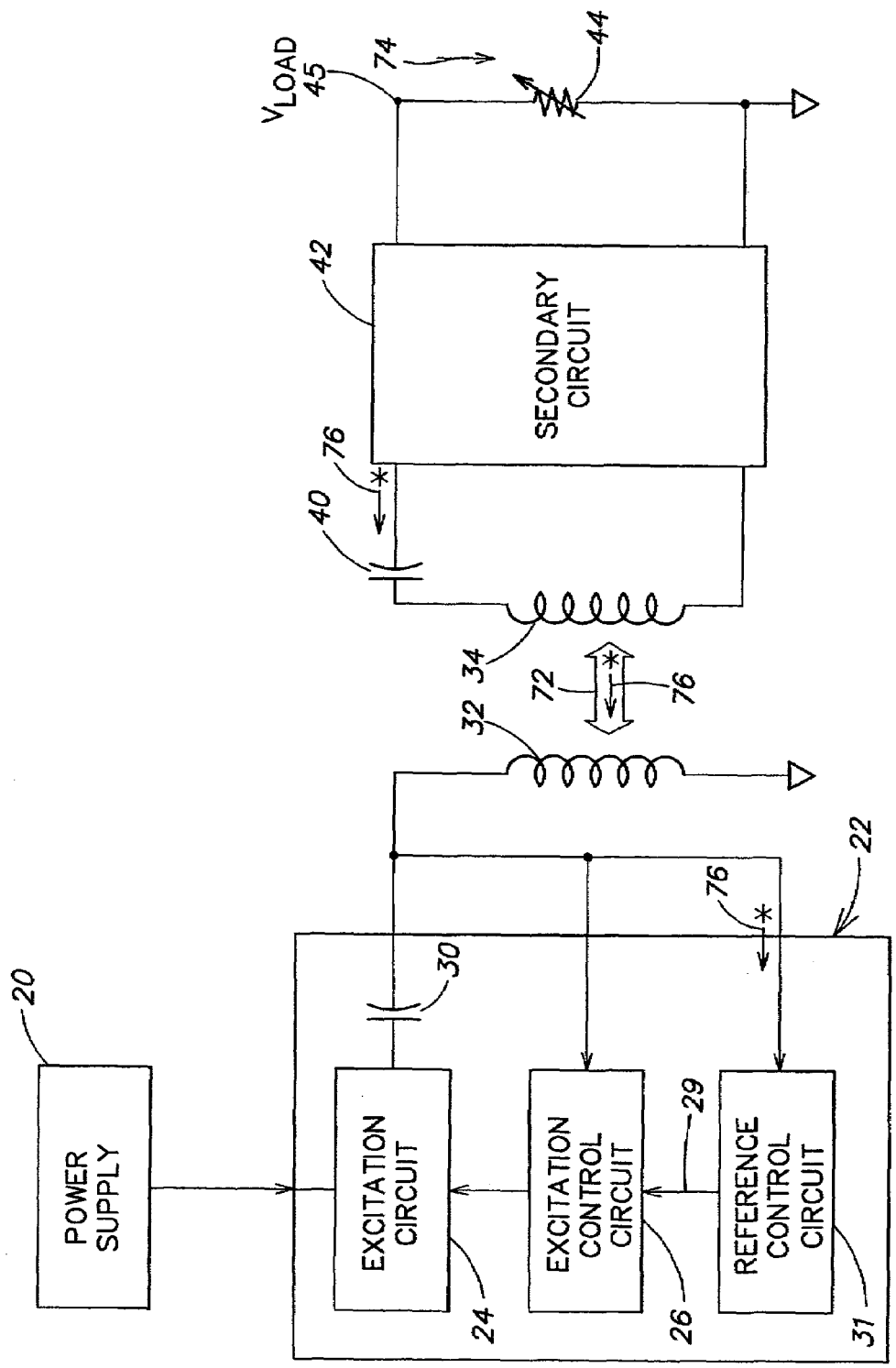
FIG. 4 is a block diagram of an energy transfer system according to another embodiment of the invention.
Figure 5:
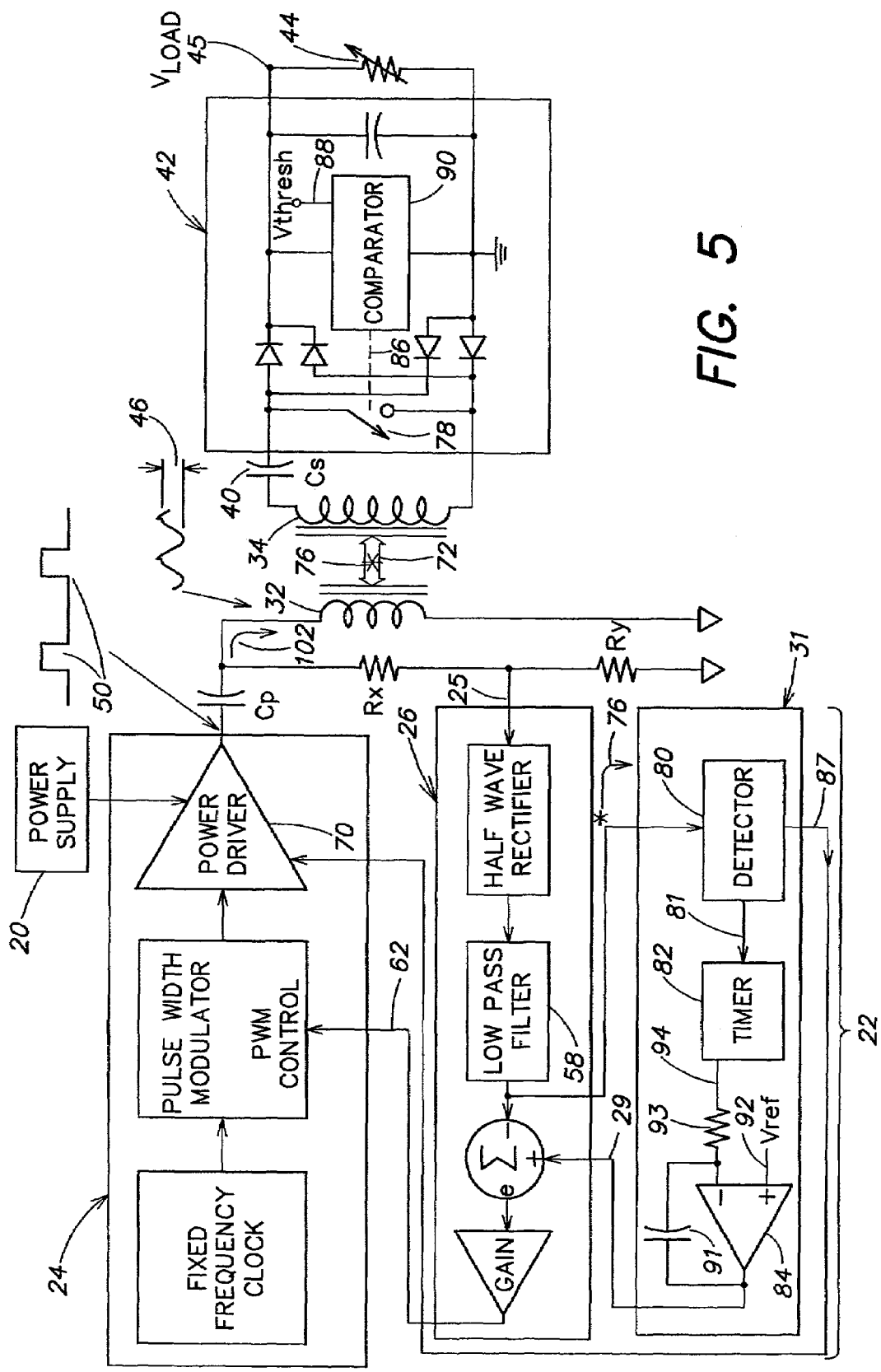
FIG. 5 is a more detailed block diagram of the energy transfer system shown in FIG. 4, according to one embodiment of the invention.

In another exemplary embodiment of the invention, as illustrated in FIGS. 4 and 5 and discussed in greater detail below, the primary amplitude of the voltage across the primary winding 32 is varied in a controlled manner, based at least in part on changes in the load and/or changes in the relative position of the primary and secondary windings of the energy transfer system, such that the load voltage is regulated near a predetermined threshold value. Accordingly, the embodiment of FIGS. 4 and 5 differs from that of FIGS. 1 and 2 at least with respect to the manner of regulation of the primary amplitude. In one aspect of this embodiment, the primary amplitude is controlled based on information related to the load that is obtained via a power channel of the energy transfer system. In some aspects, the embodiment of FIGS. 4 and 5 provides a more sophisticated implementation of an energy transfer system than does the embodiment of FIGS. 1 and 2, by regulating the load voltage within a relatively narrower range of voltages. However, it should be appreciated that both of the embodiments discussed above, as well as other embodiments of the invention, provide viable alternative solutions for a variety of energy transfer system control applications.

Another aspect of the present invention relates to the use of various embodiments of energy transfer methods and apparatus of the invention (including the above-described embodiments) in connection with the human body. In particular, one embodiment of the invention is directed to a transcutaneous energy transfer (TET) system for transferring power from a power supply external to the body to a device implanted in the body. Such an implementation places stringent requirements on the ability of the TET system to accurately and reliably unction under significant variations in load and/or relative position of the primary winding 32 and the secondary winding 34. In one aspect of this embodiment, the variable load 44 indicated in various figures may include one or more prosthetic devices implanted in a human body. Examples of such devices include, but are not limited to, artificial hearts, ventricular assist devices, cardioverter/defibrillators, infusion pumps, pacemakers, cochlear implants, and the like. In addition to any of the foregoing examples, the variable load 44 also may include a rechargeable battery that is used, for example, as a temporary backup power source in the event that power provided by the power source 20 is interrupted.

Following below are more detailed descriptions of various concepts related to, and embodiments of, methods, apparatus, and systems according to the present invention for providing a sufficiently stable power to a load in an energy transfer system. It should be appreciated that various aspects of the invention as discussed herein may be implemented in any of numerous ways, as the invention is not limited to any particular manner of implementation. Examples of specific implementations are provided for illustrative purposes only.

FIG. 1 shows that, in one embodiment, an energy transfer system of the invention includes a primary circuit 22, electrically coupled to the primary winding 32, to regulate a primary voltage across the primary winding 32. In FIG. 1, the voltage across the primary winding 32 is illustrated symbolically by an approximately sinusoidal waveform; it should be appreciated, however, that the invention is not limited in this respect, as other voltage waveforms may be suitable in various embodiments. For purposes of the following discussion, the power supply 20, the primary circuit 22, the primary winding 32, and any other components electrically coupled to the primary winding 32 may be referred to collectively as a "primary side" of the energy transfer system.

FIG. 1 also shows that, according to one embodiment, an energy transfer system of the invention includes a secondary circuit 42 electrically coupled to the secondary winding 34 and the load 44, to provide output power to the load. For purposes of the following discussion, the secondary circuit 42, the secondary winding 34, the load 44, and any other components electrically coupled to the secondary winding 34 may be referred to collectively as a "secondary side" of the energy transfer system.

In the embodiment of FIG. 1, the primary circuit 22 includes one or more capacitors 30 coupled to the primary winding 32 to form a primary resonant circuit 48 with the primary winding 32 (the primary resonant circuit 48 is indicated in FIG. 1 with dashed lines). In this embodiment, the primary circuit 22 also includes an excitation circuit 24, electrically coupled to the power supply 20 and the primary resonant circuit 48, to provide input power to the primary resonant circuit. Additionally, the primary circuit 22 of this embodiment includes an excitation control circuit 26, electrically coupled to the excitation circuit 24 and the primary winding 32, to control the excitation circuit 24 so as to modulate the input power provided to the primary resonant circuit 48.

In one aspect of the embodiment of FIG. 1, the primary circuit 22 regulates the primary amplitude 46 of the voltage across the primary winding 32 such that the primary amplitude is held essentially constant. In particular, the primary circuit 22 regulates the primary amplitude 46 by modulating the input power provided by the power supply 20 to the primary winding 32, such that the primary amplitude is maintained approximately at a value that is proportional to a fixed reference parameter. As can be seen in FIG. 1, the primary side of the energy transfer system is configured as a feedback loop that includes the excitation control circuit 26 and the excitation circuit 24. A signal associated with the primary winding 32 is monitored as one input 25 to the feedback loop. The monitored input signal is compared to a reference parameter 27 to effect control (e.g., modulation) of the input power provided to the primary resonant circuit. More specifically, the excitation control circuit 26 controls the excitation circuit 24 based on a comparison of a reference parameter 27 and a measurable characteristic of a signal associated with the primary winding 32.

In the embodiment illustrated in FIG. 1, the reference parameter 27 is generated by a fixed reference source 28. In one aspect of the embodiment shown in FIG. 1, the reference parameter 27 may be, for example, a reference voltage or a reference current provided by the fixed reference source 28. It should be appreciated, however, that the invention is not limited in this respect; namely, in another embodiment, the reference parameter 27 may be provided by a varying reference source (as discussed further below in connection with FIGS. 4 and 5).

Additionally, the measurable characteristic of a signal associated with the primary winding 32 (which is monitored as an input 25 to the primary side feedback loop of FIG. 1) may include, for example, the primary amplitude 46 of the primary voltage across the primary winding 32. However, it should be appreciated that the invention is not limited in this respect, as other measurable characteristics (e.g., current, frequency, phase) of a signal associated with the primary winding 32 may be compared by the excitation control circuit 26 to one or more of a variety of reference parameters 27 for purposes of controlling the excitation circuit 24, according to other embodiments of the invention.

In the embodiment of FIG. 1, the primary amplitude 46 may not be held precisely at a fixed value at all times by the excitation control circuit 26 and the excitation circuit 24, since feedback control generally is associated with some response time. In particular, the primary side feedback loop generally must sense some change in a signal monitored at the input 25 before effecting some control function. However, for purposes of the present discussion, it should be appreciated that the primary amplitude 46 is essentially maintained at a constant value that is proportional to the fixed reference parameter 27 as a result of the feedback control loop, with some nominal variation from the regulated value due to a response time of the feedback loop.

In one embodiment, the excitation circuit 24 of FIG. 1 outputs one or more pulses 50 to the primary resonant circuit 48 to provide the input power to the primary resonant circuit. In one aspect of this embodiment, the excitation control circuit 26 controls a width 52 of the pulses 50 output by the excitation circuit 24, such that the measurable characteristic of the signal associated with the primary winding 32 is approximately equal to a predetermined value that is proportional to the reference parameter 27. For example, in one aspect, the excitation control circuit 26 controls the width 52 of the pulses 50 such that the primary amplitude 46 is approximately equal to a predetermined amplitude that is proportional to the reference parameter 27 (e.g., a reference voltage).

FIG. 2 is a more detailed block diagram of the energy transfer system shown in FIG. 1, according to one embodiment of the invention. In the embodiment of FIG. 2, the excitation control circuit 26 monitors (at the input 25) the primary amplitude 46 of the primary voltage across the primary winding 32. Additionally, the excitation control circuit 26 controls the excitation circuit 24, based only on the monitored primary amplitude and the reference parameter 27 (e.g., a reference voltage), so as to regulate the primary amplitude 46 of the voltage across the primary winding 32 (which forms part of the primary resonant circuit 48 shown in FIG. 1). In the embodiment of FIG. 2, the reference parameter 27 is selected such that the primary amplitude 46 is regulated to provide a sufficiently stable output power to the variable load 44 notwithstanding changes in the load and/or relative position of the primary and secondary windings, as discussed further below. FIG. 2 also identifies a load voltage 45 ($V_{load}$) across the load 44 and a load current 74 through the load 44.

In one aspect of the embodiment shown in FIG. 2, the excitation control circuit 26 controls the excitation circuit 24 such that the primary voltage has essentially a constant frequency 54. The constant frequency 54 may be selected based on a resonant frequency of the primary resonant circuit formed by one or more capacitors 30 and the primary winding 32. In one embodiment, one or more capacitors 30 are selected such that the resonant frequency of the primary resonant circuit approximates that of a resonant frequency of a secondary resonant circuit formed by the secondary winding 34 and one or more capacitors 40 coupled to the secondary winding, as discussed further below.

In the embodiment of FIG. 2, the primary amplitude 46 is monitored by the excitation control circuit 26 via a resistor divider network, shown symbolically in FIG. 2 by the resistors $R_x$ and $R_y$. In the excitation control circuit 26, the monitored primary amplitude is rectified by a half wave rectifier 56 and then filtered by a low pass filter 58. A comparator 60 then compares the rectified and filtered monitored primary amplitude to the reference parameter 27 to generate an excitation control signal 62 that controls the excitation circuit 24. For example, in one aspect, the comparator 60 is a difference amplifier, the output of which varies continuously in proportion with a difference between its inputs (e.g., the rectified and filtered monitored primary amplitude and the reference parameter 27).

As shown in FIG. 2, in one embodiment, the excitation circuit 24 includes a fixed frequency clock 64 that serves as a frequency reference for a pulse width modulator 66. The pulse width modulator 66 receives the excitation control signal 62 output by the excitation control circuit 26 and outputs a power driver control signal 68 to a power driver 70. The power driver 70 provides power from the power supply 20 to the primary resonant circuit (formed by one or more capacitors 30 and the primary winding 32) in the form of the pulses 50, which periodically inject energy into the primary resonant circuit.

In FIG. 2, the pulse width modulator 66 controls the width 52 of the pulses 50 based on the excitation control signal 62. In particular, according to one aspect of this embodiment, a wider pulse width 52 supplies greater power to the primary resonant circuit, thereby increasing the primary amplitude 46, whereas a shorter pulse width 52 provides less power to the primary resonant circuit, thereby decreasing the primary amplitude 46. In this manner, the power provided to the primary resonant circuit is controlled based on a comparison of the primary amplitude 46 and the reference parameter 27.

Figure 3A:
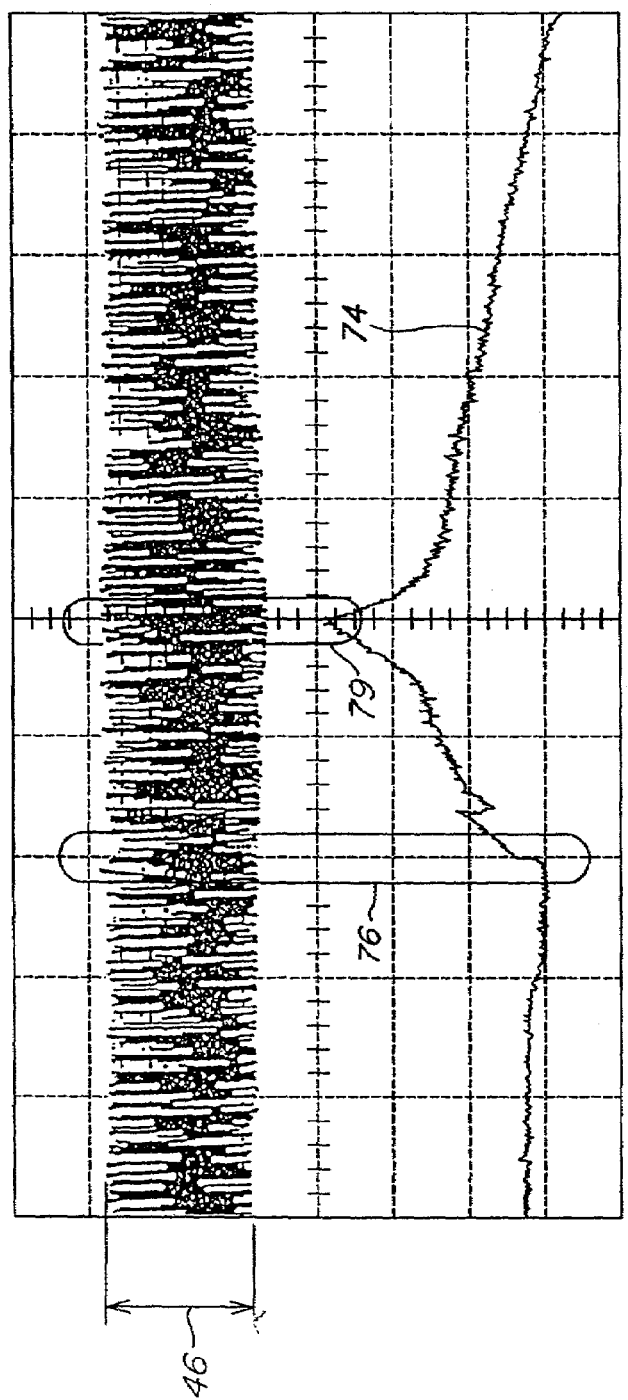
FIGS. 3A, 3B, and 3C are graphs that each show a plot of a primary voltage across a primary winding of the energy transfer system of FIG. 2 as a function of time, and a corresponding current through a load, according to one embodiment of the invention.
Figure 3B:
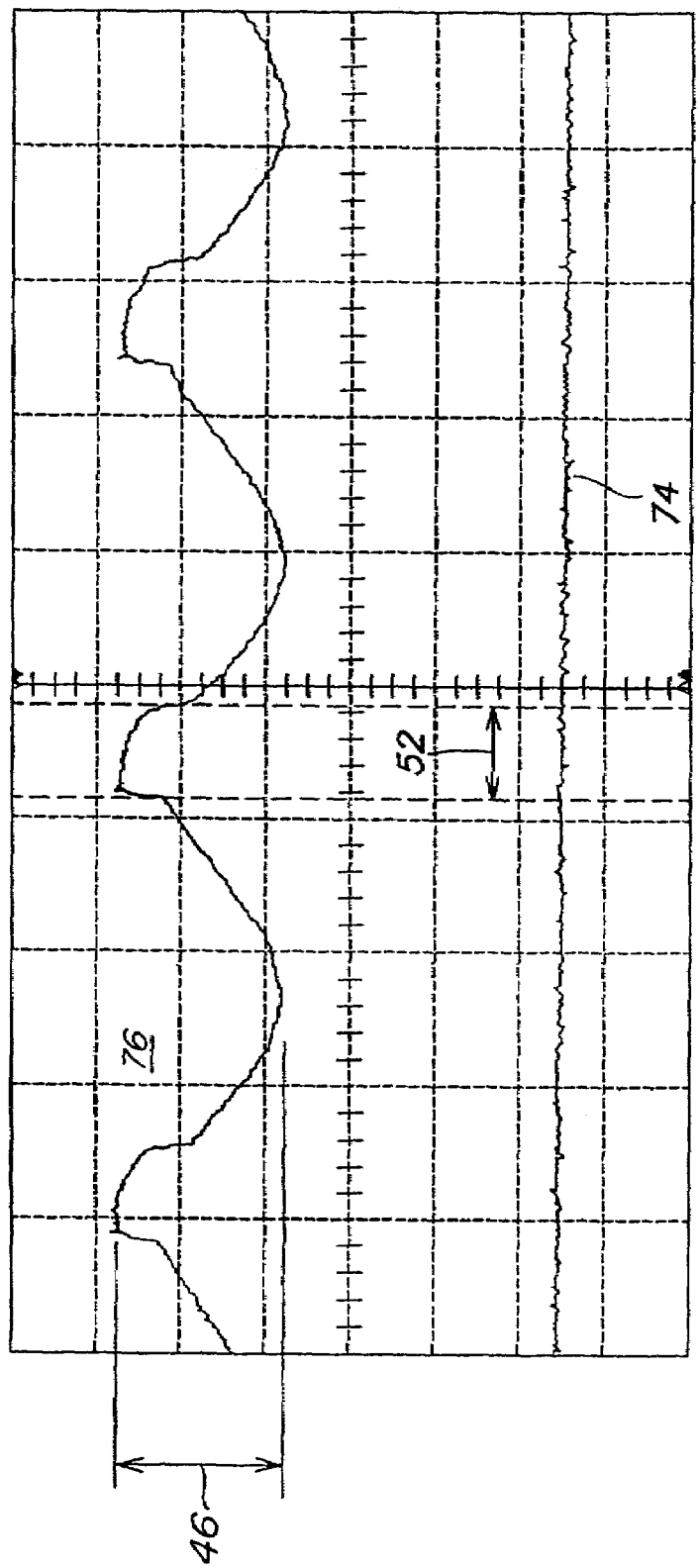
Figure 3C:
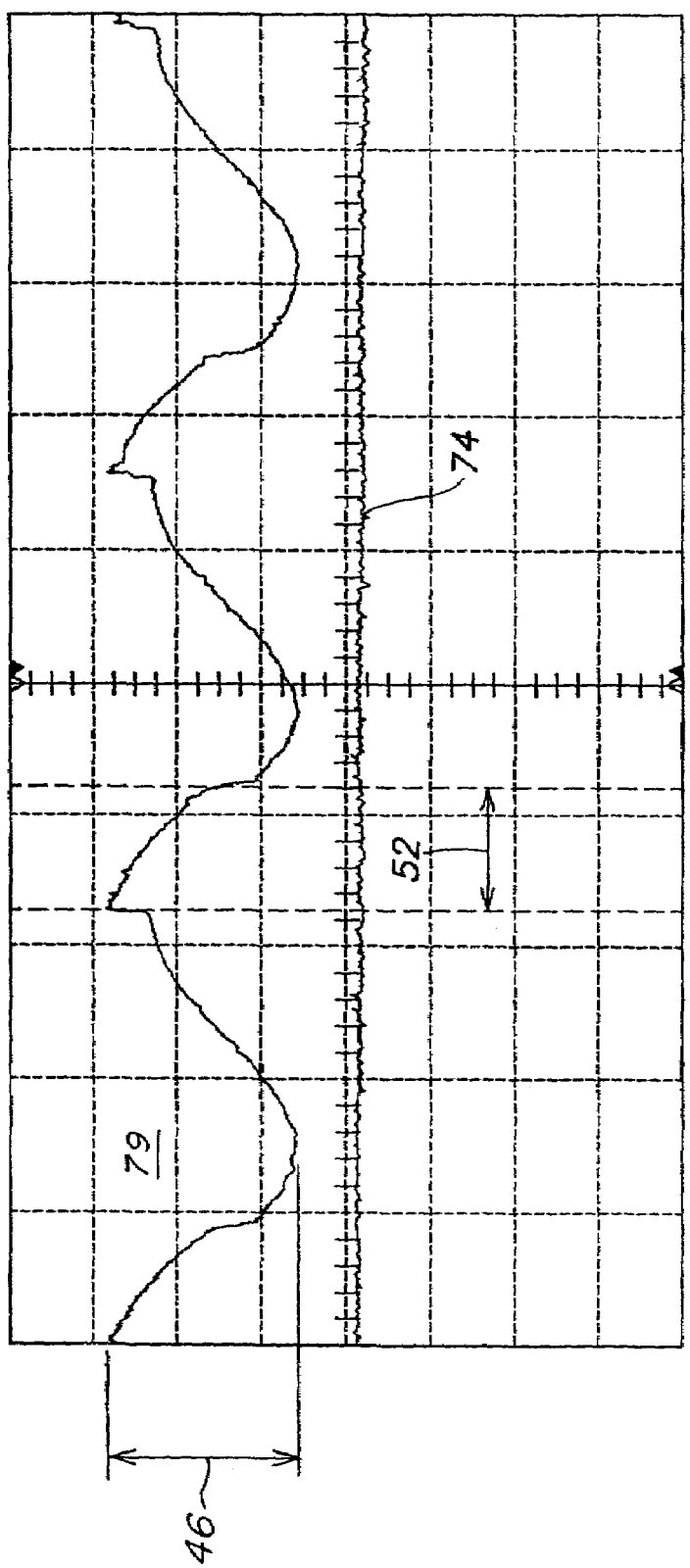

FIGS. 3A, 3B, and 3C are graphs that each show plots of the voltage across the primary winding 32 as a function of time (respective top plots), and a current 74 through the load 44 as a function of time (respective bottom plots) during operation of the energy transfer system shown in FIG. 2. In the graph of FIG. 3A, it can be seen from the bottom plot that the load 44 coupled to the secondary winding 34 may vary, as illustrated by the variations in the load current 74; accordingly, the load 44 may have different power requirements from time to time. Generally, changes in the variable load 44 (i.e., varying power requirements) are observable as changes in a secondary voltage across the secondary winding 34. Such changes in the secondary voltage in turn may be observed as changes in the primary amplitude 46 of the primary voltage, as illustrated in the graphs of FIGS. 3A, 3B, and 3C, by virtue of the magnetic coupling between the primary winding 32 and the secondary winding 34.

The graph of FIG. 3B is a horizontally expanded view (smaller time scale per horizontal division) of the region 76 in the graph of FIG. 3A. In the region 76, the load current 74 is at a minimum (i.e., the load requires relatively less power). Similarly, the graph of FIG. 3C is a horizontally expanded view of the region 79 in the graph of FIG. 3A, at which point the load current 74 is at a maximum (i.e., the load requires relatively more power).

As illustrated in the graph of FIG. 3B, when the load requires relatively less power, the excitation control circuit 26 monitors (i.e., senses) an initial increase in the primary amplitude 46 due to the "lighter" load, and in response controls the excitation circuit 24 such that the pulse width 52 of the pulses 50 provided to the primary resonant circuit (which can be viewed as artifacts in the sinusoidal waveform in the graph of FIG. 3B) is decreased, resulting in a corresponding decrease in the primary amplitude 46. In contrast, as illustrated in the graph of FIG. 3C, when the load requires relatively more power, the excitation control circuit 26 monitors an initial decrease in the primary amplitude 46 due to the "heavier" load, and in response controls the excitation circuit 24 such that the pulse width 52 is increased, resulting in a corresponding increase in the primary amplitude 46. In both cases, the primary amplitude 46 is regulated based on the reference parameter 27 to essentially a constant value, with nominal variations from this value due to a response time of the circuits constituting the primary side feedback control loop (e.g., the excitation circuit 24 and the excitation control circuit 26).

As discussed above, the energy transfer systems shown in FIGS. 1 and 2 regulate the primary amplitude 46 to provide a sufficiently stable output power to the load 44 essentially independently of system conditions associated with the secondary side of the energy transfer system. In particular, in one aspect of this embodiment, regulation of the primary amplitude does not necessarily depend upon changes in the load and/or changes in relative position of the windings. Instead, by selecting an appropriate reference parameter 27, the primary amplitude 46 is regulated such that a sufficiently stable power is provided to the load over a predetermined range for the load voltage 45, which may fluctuate due to changes in the load and/or changes in the relative position of the primary and secondary windings.

In particular, in one aspect of the embodiment of FIGS. 1 and 2, a suitable desired range for the load voltage 45 is empirically determined based on expected operating characteristics and power requirements of the load and particular design parameters of the energy transfer system. In this aspect, the desired range for the load voltage 45 generally takes into consideration nominal changes in the load (i.e., different power requirements from time to time) and changes in the relative position of the windings that may occur from time to time during normal operation of the system in a particular application. The reference parameter 27 for the primary amplitude 46 is selected based on the desired range for the load voltage 45, such that the load voltage falls essentially within the desired range when the primary amplitude is regulated to a value that is proportional to the reference parameter.

Although the load voltage 45 in the embodiment of FIGS. 1 and 2 may be susceptible to minor fluctuations due to changes in the load and/or relative position of the windings notwithstanding the regulation of the primary amplitude, it should be appreciated that this embodiment nonetheless provides an acceptable solution for a variety of energy transfer system control applications with appropriate selection of the reference parameter 27. In particular, it should be appreciated that at least one favorable feature of this embodiment is simplicity of implementation while nonetheless providing sufficient control of the energy transfer system.

FIG. 3D is a circuit diagram showing one example of an electronic circuit implementation of a primary side of the energy transfer system shown in FIG. 2, according to one embodiment of the invention. In FIG. 3D, the power source 20 is shown as 24 Volts supplied to a terminal of one of two power transistors Q2 and Q3 that constitute a portion of the power driver 70. The 24 Volt power source may be supplied, for example, by a suitable battery.

In one aspect of the embodiment of FIG. 3D, a target amplitude for the primary amplitude 46 is in a range of from approximately 100 Volts peak-to-peak to approximately 200 Volts peak-to-peak. In this aspect, the capacitor 30 of the primary resonant circuit 48 shown in FIGS. 1 and 2 is implemented by capacitors C4, C7, C9, and C23. The MOSFET drivers Q2 and Q3 switch between the power source 20 and a ground potential, resulting in a 24 Volt peak-to-peak essentially rectangular wave drive signal which is amplified by the primary resonant circuit 48. The gates of the power transistors Q2 and Q3 are driven by integrated circuit U3. In this embodiment, the primary amplitude 46 is regulated by adjusting a pulse width of the signals that are applied to the gates of the power transistors Q2 and Q3, as discussed in greater detail further below.

In the circuit shown in FIG. 3D, an exemplary frequency source for the fixed frequency clock circuit 64 is shown as a 10 MHz crystal oscillator, which is divided down by counter U9 to approximately 312.5 kHz. Alternatively, as discussed below in connection with another embodiment shown in FIG. 10, an adjustable RC oscillator may be employed to accommodate various resonant frequencies of the primary resonant circuit 48. Timer U8A reduces a square wave output from U9 to a narrow trigger pulse, which is output to U1 of the pulse width modulator 66.

In FIG. 3D, the primary amplitude 46 is sensed via a resistor divider network formed by resistor R6 in series with resistor R11 and variable resistor R19. The sensed signal is half-wave rectified by diode D5, filtered by resistor R10 and capacitor C19, and buffered by unity gain amplifier U4A. Amplifier U4B forms part of the comparator 60 (e.g., a difference amplifier) to provide the excitation control signal 62. The amplifier U4B compares the rectified and filtered monitored primary amplitude signal to fixed reference 27, which in this example is a 2.5 Volt reference provided by the reference source circuit 28, including Zener diode D6.

An error signal output by the amplifier U4B in FIG. 3D is limited by diode D9 and resistors R18 and R12 and buffered by amplifier U4C to produce the control signal 62. According to one aspect, the error signal is limited by the diode and resistors so as to limit the pulse width 52 of the signal 68 output from the pulse width modulator 66 to a maximum of 50% duty cycle. This is done because maximum power transfer to the primary resonant circuit occurs at 50% duty cycle. If the pulse width were allowed to increase beyond 50% duty cycle, the primary amplitude would then be allowed to decrease as the error signal increased, effectively delivering less power to the primary resonant circuit when the feedback loop was trying to command more power, so as to increase the primary amplitude.

The control signal 62 in FIG. 3D is applied to a voltage controlled timer U1 which forms part of the pulse width modulator 66. In the embodiment of FIG. 3D, if the rectified and filtered monitored primary amplitude input to U4B of the comparator 60 is lower than the reference voltage 27, the control signal 62 increases, causing a width of pulses in the output signal 68 of the timer U1 to increase. Conversely, if the rectified and filtered monitored primary amplitude input to U4B of the comparator 60 is higher than the reference voltage 27, the control signal 62 decreases, causing a width of pulses in the output signal 68 of the timer U1 to decrease. The decreased pulse width in turn decreases the primary amplitude 46.

FIG. 4 is a block diagram similar to that of FIG. 1, showing an example of an energy transfer system according to another embodiment of the invention. In the energy transfer system of FIG. 4, the fixed reference source 28 in the primary circuit 22 of FIGS. 1 and 2 is replaced by a reference control circuit 31, which outputs a varying reference parameter 29 based on a measurable characteristic of a signal associated with the primary winding 32 (e.g., the primary amplitude 46). In this manner, the embodiment of FIG. 4 differs from that of FIGS. 1 and 2, in that the primary amplitude 46 may be varied in a controlled manner rather than regulated to an essentially constant value. Additionally, in the embodiment of FIG. 4, the measurable characteristic on which the varying reference parameter 29 is based may include some indication of changes in the load and/or changes in relative position of the primary and secondary windings. Accordingly, in one aspect, the embodiment of FIG. 4 actively controls (e.g., varies) the primary amplitude 46 in response to changes in the load and/or relative winding position.

In one aspect of the embodiment of FIG. 4, the magnetic field 36 that couples the primary and secondary windings is viewed as forming a portion of a "power channel" 72, over which power is transferred from the power supply 20 to the variable load 44 at the particular frequency 54, as illustrated in FIGS. 1 and 2 (e.g., approximately the resonant frequency of the primary and secondary resonant circuits). With reference again for the moment to FIG. 1, while power typically is transferred in a direction illustrated symbolically by the arrows of the magnetic field 36, Applicants have appreciated that information related to the secondary side of the energy transfer system, including information related to changes in the variable load 44 and/or changes in relative winding position, may be communicated in an opposite direction (i.e., from the secondary winding to the primary winding) via the power channel 72.

In view of the foregoing, according to one aspect of the energy transfer system shown in FIG. 4, the secondary circuit 42 of the secondary side of the energy transfer system generates one or more indications 76 (shown symbolically as an asterisk in FIG. 4) on the power channel 72 that are detectable on the primary side of the energy transfer system. One or more detectable indications 76 provide information to the primary circuit 22 that is related, for example, to the variable load 44 and the relative position of the windings. In one aspect of this embodiment, the reference control circuit 31 includes circuitry to detect a detectable indication 76 on the power channel 72, as discussed further below in connection with FIGS. 5 and 10, and in turn outputs the varying reference parameter 29 based on one or more detectable indications 76.

According to another aspect of this embodiment, as discussed further below in connection with FIG. 5, the secondary circuit 42 of FIG. 4 provides one or more detectable indications 76 on the power channel 72 when the load voltage 45 ($V_{load}$) across the variable load 44 exceeds a predetermined threshold load voltage. In response to one or more detectable indications 76, the primary circuit 22 regulates the primary amplitude 46 such that the load voltage 45 approximates the predetermined threshold load voltage, notwithstanding changes in the variable load and/or changes in the relative position of the windings.

Figure 6:
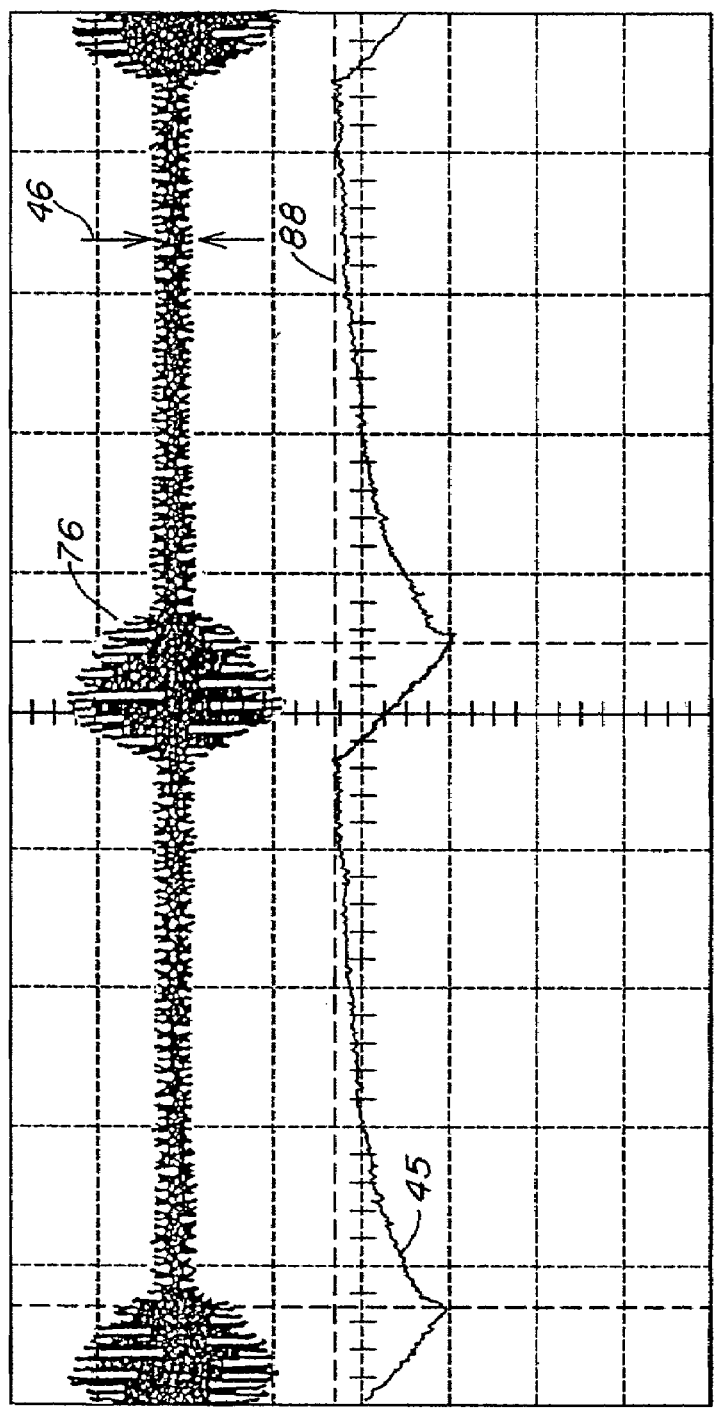
FIG. 6 is a diagram showing an example of a detectable indication on a power channel of the energy transfer system of FIG. 5, which indication is used to regulate voltages in the energy transfer system, according to one embodiment of the invention.

FIG. 5 is a more detailed block diagram of the energy transfer system shown in FIG. 4, according to one embodiment of the invention. In one aspect of the embodiment of FIG. 5, detectable indications 76 on the power channel 72 include one or more surges that are observable in the primary amplitude 46 of the primary voltage across the primary winding 32. FIG. 6 shows an example of detectable indications 76 on the power channel 72, in the form of surges that are observable in the primary amplitude 46. It should be appreciated, however, that the invention is not limited to the example of a detectable indication shown in FIG. 6, and that other types of detectable indications, as well as methods and apparatus for generating and detecting such indications, may be implemented according to other embodiments of the invention.

In the embodiment of FIG. 5, the secondary circuit 42 includes a comparator 90 to make a comparison of the load voltage 45 across the variable load 44 and a predetermined threshold voltage 88 ($V_{thresh}$). An output of the comparator 90 is coupled to a surge generator 78 (shown symbolically in FIG. 5 as a switch) which generates one or more surges on the power channel 72, based on the comparison of the load voltage 45 and the predetermined threshold load voltage 88.

In one aspect of the embodiment of FIG. 5, the surge generator 78 may include a shunt circuit, for example, in the form of a switch, that diverts the output power provided by the secondary winding 34 away from the variable load 44 when an input signal 86 to the shunt circuit (output by the comparator 90) reaches a shunt activation level. In one embodiment, the comparator 90 generates the input signal 86 having the shunt activation level when the load voltage 45 exceeds the predetermined threshold load voltage 88.

In FIG. 5, as the shunt circuit is activated, the combination of the capacitive load due to one or more capacitors 40 and the resistive load due to the load 44 is replaced by the capacitive load due to the one or more capacitors 40 in series with the self-inductance of the secondary winding 34. The activation of the shunt circuit creates a short circuit across the resonant circuit formed by the one or more capacitors 40 and the secondary winding 34. This, in turn, results in a surge in the current in the secondary winding. The surge thus generated propagates via the power channel 72 and is observable in the primary voltage.

According to one aspect of the energy transfer system of FIG. 5, the primary circuit 22 (comprising the excitation circuit 24, the excitation control circuit 26, and the reference control circuit 31) regulates the primary amplitude 46 such that the input signal 86 to the surge generator 78 (e.g., the shunt circuit) approximates and substantially remains below the shunt activation level (e.g, the input signal 86 may be slightly above the shunt activation level for a relatively short time, but for the most part the input signal 86 remains below the shunt activation level). Stated differently, the primary amplitude 46 is regulated such that the shunt circuit has a relatively small activation duty cycle, so as to reduce any output power that may be dissipated through the shunt circuit rather than provided to the variable load. In some applications, a diversion of output power through the shunt circuit for a significant time period may produce undesirable heating in proximity to the variable load 44 (e.g., in applications where the variable load 44 may be an implanted prosthesis in a human). Accordingly, in one aspect, the energy transfer system of FIG. 5 reduces such undesirable heating by regulating the primary amplitude 46 such that the shunt circuit is activated for a relatively small portion of the time between successive activations (i.e., a relatively small activation duty cycle).

For purposes of the present discussion, in one aspect the terms "relatively small activation duty cycle" represent a time duration for activation of the shunt circuit that is insufficient to achieve regulation of the load voltage via operation of the secondary circuit 42 alone. In another aspect of the embodiment of FIG. 5, the primary amplitude 46 is regulated such that the secondary circuit has an activation time of less than approximately 100 microseconds, and consecutive activations of the secondary circuit occur approximately every 2 to 3 milliseconds. Alternatively, in yet another aspect, the primary amplitude 46 is regulated such that the surge generator 78 (e.g., the shunt circuit) has a duty cycle of less than approximately 1% (i.e., the shunt circuit is activated for less than approximately 1% of the time between consecutive activations of the shunt circuit). In yet another aspect, the primary amplitude 46 is regulated such that the shunt circuit has a duty cycle of less than approximately 0.5%. In yet another aspect, the primary amplitude 46 is regulated such that the shunt circuit has a duty cycle of less than approximately 0.1%, so as to reduce power dissipation through the shunt circuit.

To monitor and respond to a detectable indication 76 on the power channel 72 provided by the secondary circuit 42, FIG. 5 shows that the reference control circuit 31 includes a detector circuit 80, coupled to an output of the low pass filter 58 of the excitation control circuit 26, to detect the detectable indication and to provide a detected indication signal 81. In the embodiment of FIG. 5, the reference control circuit 31 also includes a timer 82 coupled to the detector circuit 80 to receive the detected indication signal 81. Additionally, the reference control circuit 31 of FIG. 5 includes an output circuit 84 coupled to the timer to output the varying reference parameter 29 based at least on the detected indication signal 81. It should be appreciated, however, that the reference control circuit 31 is not limited to the implementation shown in FIG. 5; in particular, in another embodiment discussed below in connection with FIG. 11, the timer 82 and the output circuit 84 may be replaced by alternative circuitry.

With reference again to FIG. 5, the output circuit 84 in this embodiment is shown as an integrator having a time constant based on capacitor 91 and resistor 93. In one aspect, the timer 82 controls the integrator such that the integrator outputs the varying reference parameter as a varying reference voltage having an essentially triangular waveform. In another aspect, values for the capacitor 91 and the resistor 93, as well as values for components associated with the timer 80 (as illustrated, for example, in FIG. 10) are chosen such that the varying reference parameter 29 has a frequency in a range of from approximately 5 Hz to approximately 40 Hz, as discussed further below.

According to one embodiment of the invention, the reference control circuit 31 shown in FIG. 5 functions as follows. The detector 80 monitors the rectified and filtered primary amplitude for one or more detectable indications 76 (e.g., one or more surges), and if a detectable indication is detected, the detector outputs a detected indication signal 81 which triggers the timer 82. The timer 82 outputs a timer output signal 94 to a first input of the output circuit 84, which signal switches between a high level and a low level. In particular, once the timer is triggered by the detected indication signal 81, the timer output signal 94 goes to the high level for a fixed time. The timer 82 may be triggered one or more times by the detected indication signal 81, and the timer output signal 94 remains at the high level if the detectable indications continue to be detected.

In FIG. 5, a second input of the output circuit 84 receives a reference voltage 92 (labeled as $V_{ref}$ in FIG. 5), which voltage is between the high and low levels of the timer output signal 94. For example, in one aspect of this embodiment, the voltage $V_{ref}$ is set to approximately midway between the high and low timer output levels. While the timer output signal 94 is at the high level (i.e., above the reference voltage 92), the varying reference parameter 29 (e.g., a varying voltage in this example) output by the output circuit 84 ramps downward at a rate that is related to the respective values of the capacitor 91 and the resistor 93. Since the varying reference parameter 29 ramps downward, the primary amplitude 46 ramps downward as well to track the changes in the varying reference parameter. When the primary amplitude 46 is reduced such that the load voltage 45 is less than the threshold voltage 88 in the secondary circuit 42, the secondary circuit 42 stops generating the detectable indications 76 and, accordingly, the detector 80 stops triggering the timer 82.

The integrating output circuit 84 of FIG. 5 continues ramping down until the timer 82 resets the timer output signal 94 to the low level. The timer 82 may be implemented so as to have a variety of possible reset times and duty cycles, as discussed further below in connection with FIGS. 7 and 10. Once the timer resets the timer output signal 94 to the low level, the signal 94 is below the reference voltage 92; hence, the integrating output circuit 84 begins ramping up the varying reference parameter 29 (at a rate that is related to the respective values of the capacitor 91 and the resistor 93). Accordingly, it should be appreciated that one or more of the reference voltage 92, the component values of the capacitor 91 and the resistor 93, and the duty cycle of the timer 82, may be selected to implement various timings/waveforms for the varying reference parameter 29. For example, as discussed above, the reference voltage 92 may be selected to be half-way between the high and low levels of the timer output signal 94, so as to implement an essentially triangular waveform for the varying reference parameter 29. It should also be appreciated, however, that the invention is not limited in this respect, as other analog and/or digital circuits may be implemented to output other waveforms for the varying reference parameter 29, as discussed further below.

In the embodiment of FIG. 5, as the varying reference parameter 29 ramps upward, the primary amplitude 46 increases to track the increasing varying reference parameter, until the load voltage 45 approaches and approximates the threshold voltage 88 in the secondary circuit 42. At this point, the secondary circuit 42 generates another detectable indication 76, and the foregoing process is repeated. Accordingly, the system of FIG. 5 is capable of regulating the load voltage 45 in response to changes in the load and/or changes in relative position of the primary and secondary windings because regardless of either or both of these changes, the primary circuit 22 continuously seeks to adjust the primary amplitude 46 based on the detectable indications 76 (i.e., such that the load voltage 45 approaches and approximates the threshold voltage 88 in the secondary circuit 42).

Figure 7:
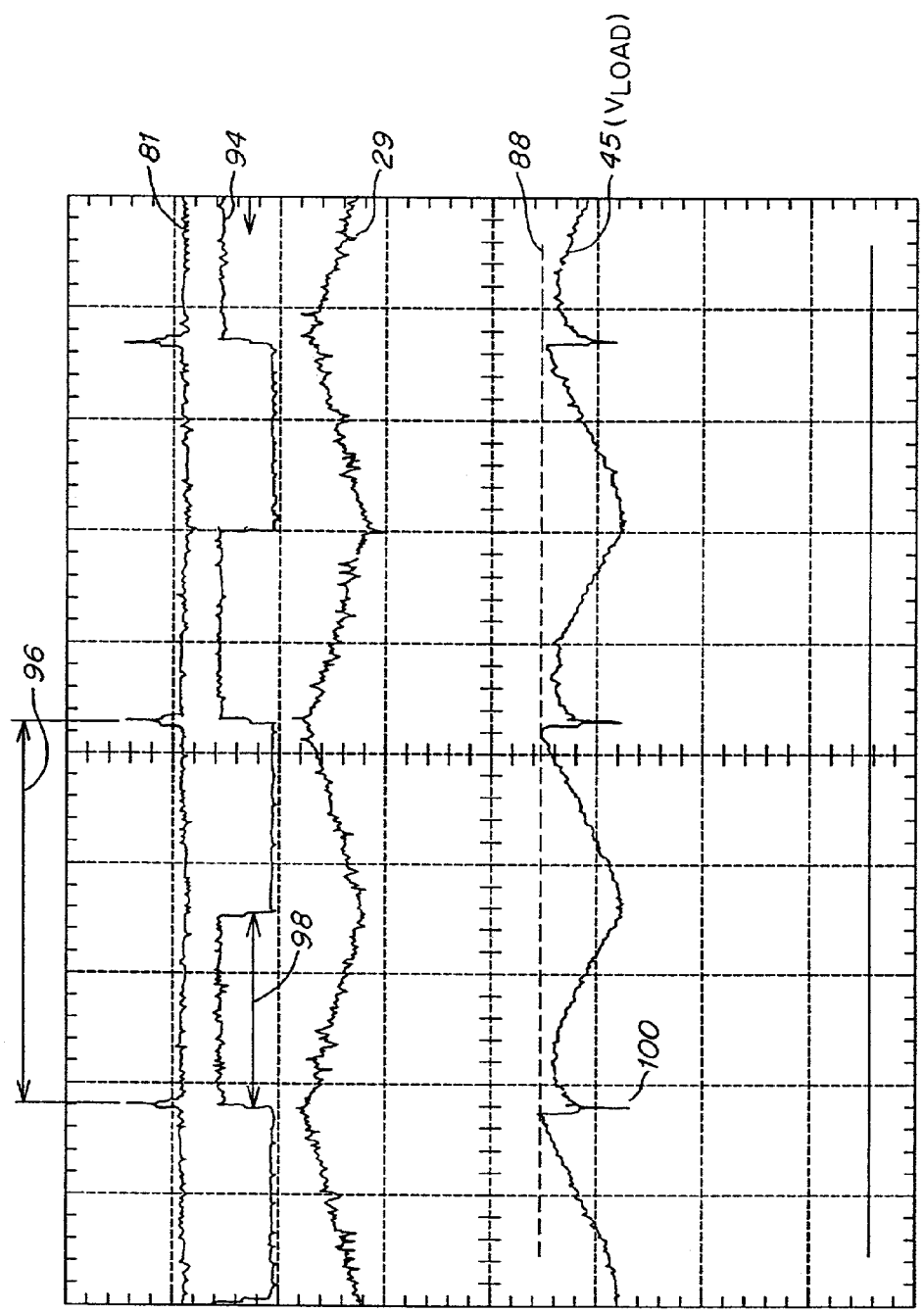
FIG. 7 is a graph showing plots of various signals in the energy transfer system of FIG. 5, according to one embodiment of the invention.

FIG. 7 is a graph showing plots of examples of various signals in the energy transfer system of FIG. 5 during the above-described regulation process, according to one embodiment of the invention. For example, the top-most plot in FIG. 7 illustrates the detected indication signal 81, the next lower plot illustrates the timer output signal 94, the next lower plot illustrates the varying reference parameter 29 (which in one example is a varying voltage), and the bottom-most plot illustrates the load voltage 45 ($V_{load}$) that results from the above-described regulation process.

With reference to FIG. 7, according to one embodiment, a frequency of the timer output signal 94 (i.e., the inverse of a period 96 of the timer output signal) and, hence, a fundamental frequency of the varying reference parameter 29, generally is selected to be fast enough so that the primary circuit 22 may effectively respond to changes in the load and/or changes in the relative position of the windings, which changes may require significant changes to the primary amplitude 46. However, in one aspect, the frequency of the timer output signal 94 is selected to additionally take into account that higher activation frequencies of the surge generator 78 of the secondary circuit 42 may produce undesirable power dissipation and excessive heating in some applications. Accordingly, at least two relevant criteria (i.e., practical response time given a particular application and power dissipation in the secondary side of the energy transfer system) may be considered in selecting an appropriate frequency for the timer output signal 94. In some instances, the frequency of the timer output signal 94 may be determined empirically, depending on the particular application of the energy transfer system. For example, in one embodiment, the frequency of the timer output signal 94 is selected to be in a range of from approximately 5 Hz to approximately 40 Hz.

With reference again to FIG. 5, in yet another embodiment, the varying reference parameter 29 is reduced immediately following detection of a detectable indication rather than ramping down, as is accomplished by the integrating output circuit 84 shown in FIG. 5. To this end, the output circuit 84 may be configured to output a saw-tooth waveform for the varying reference parameter (i.e., rapid fall, slow rise). In one aspect of this embodiment, the output circuit 84 may be implemented as a micro-controller that is configured so as to output a saw-tooth waveform based on one or more detectable indications, as opposed to the essentially triangular waveform output by the example of the integrating output circuit shown in FIG. 5. In particular, by implementing such a micro-controller, the primary circuit can rapidly reduce the primary amplitude 46 and then gradually increase it at a much slower rate. At least one advantage of implementing a micro-controller so as to provide a saw-tooth waveform varying reference parameter 29 is to safeguard against rapid variations in the load 44 which can potentially lead to harmful voltage spikes.

Yet another variation of this scheme is to initiate a time varying, adaptive rate for the increase or decrease of the primary amplitude 46. For example, upon detecting one or more indications 76 on the primary side (i.e., the detector 80 of the reference control circuit 31 provides the detected indication signal 81), each successive indication in a series of indications could be made to correspond to a larger step reduction in primary amplitude, and, as the indications stop, the rate of increase of the primary amplitude 46 could be made to increase as time passes. This scheme allows for fine adjustment of the primary amplitude around any given operating point, as well as the rapid convergence of the primary amplitude to a different operating point in case of an abrupt change of the load 44 or an abrupt change in relative winding position.

In another embodiment of the energy transfer system shown in FIG. 5, an auxiliary output of the detector 80 is connected to an auxiliary input of the power driver 70. In this manner, the detector 80 may provide a squelch signal 87 to the power driver 70 so as to reduce a surge current in the primary winding 32 upon the detection of one or more detectable indications 76 (e.g., surges) on the power channel 72. Accordingly, the squelch signal 87, along with the excitation control signal 62 provided by the excitation control circuit 26, may be employed to further regulate the primary amplitude 46.

Figure 8A:
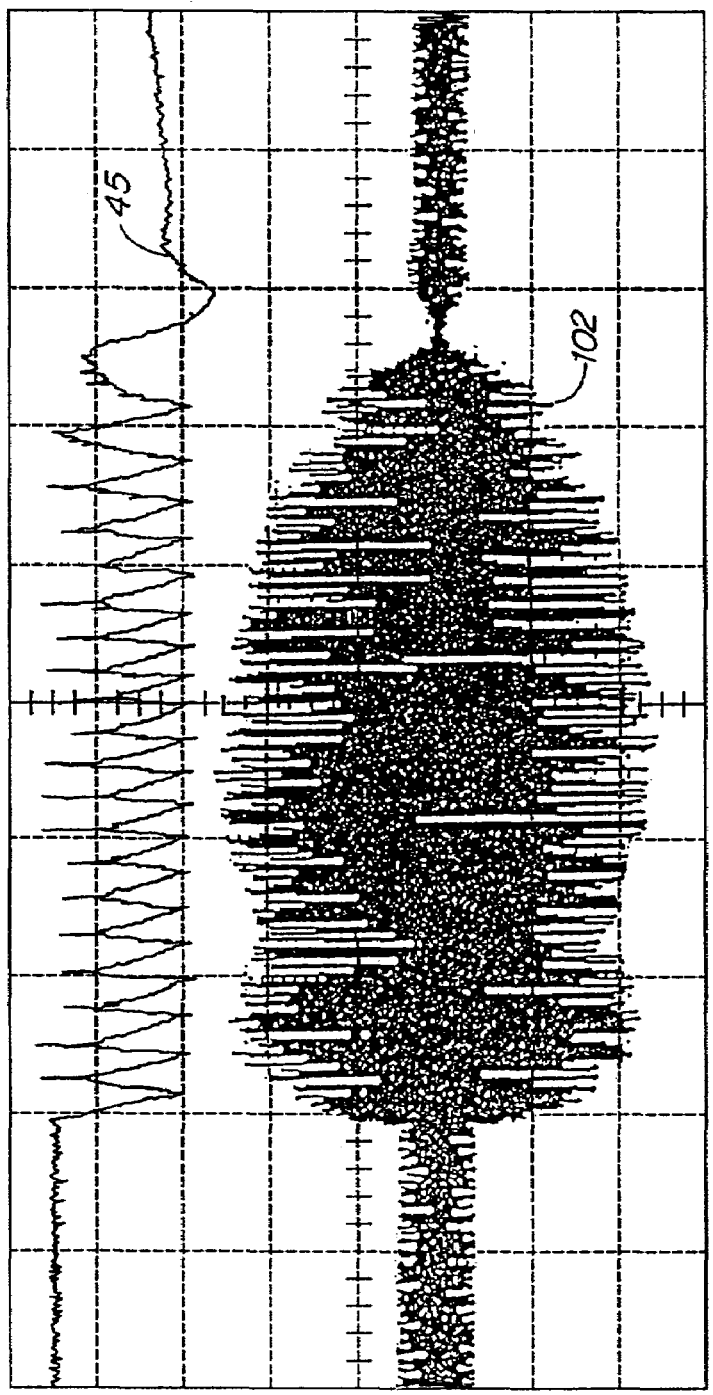
FIGS. 8A and 8B are graphs that each show plots of a load voltage and a current through a primary winding in the energy transfer system of FIG. 5, according to one embodiment of the invention.
Figure 8B:
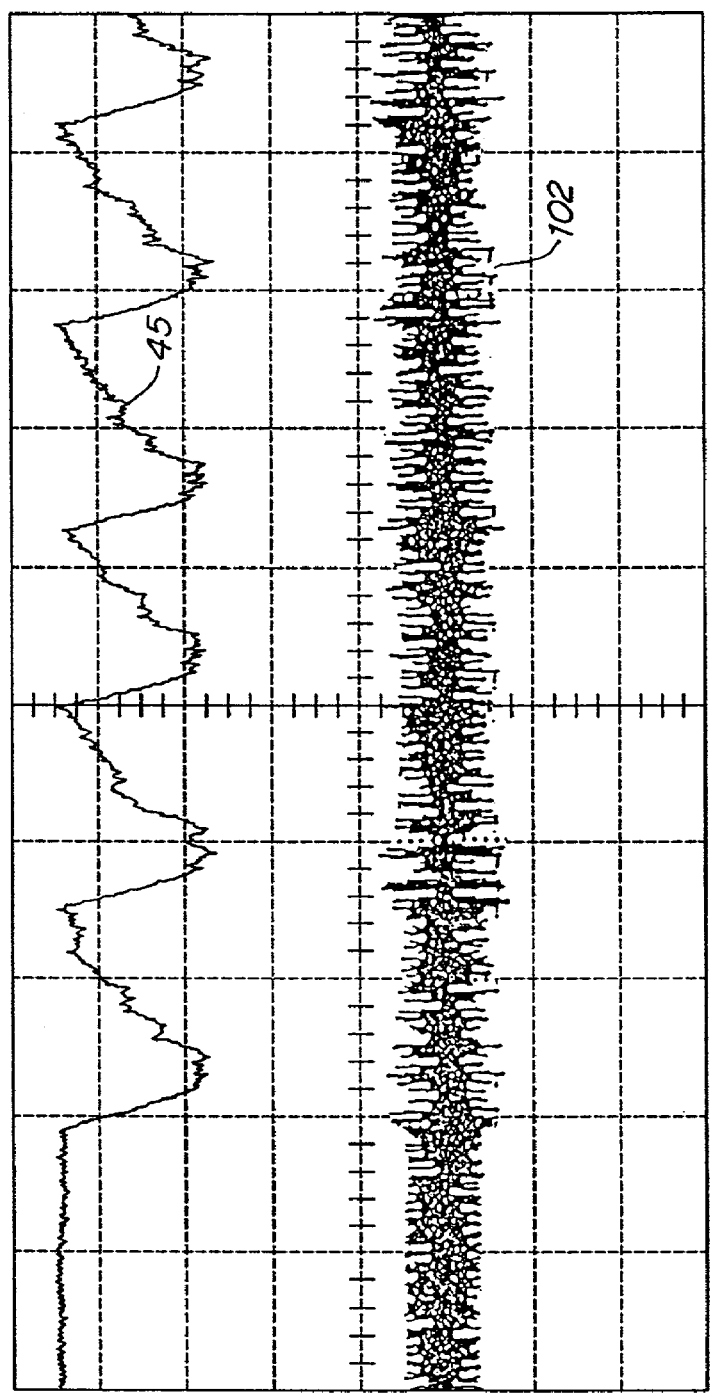

FIGS. 8A and 8B are graphs illustrating the operation of the squelch signal 87. Each of the graphs in FIGS. 8A and 8B shows the load voltage 45 (respective top plots) and a current 102 through the primary winding 32 (respective bottom plots) during a time period indicated by the reference character 100 shown in FIG. 7, namely, near and during the generation of a detectable indication or surge on the power channel. The graph of FIG. 8A represents the load voltage and the current through the primary winding if the squelch signal 87 is not used, whereas the graph of FIG. 8B represents the load voltage and the current through the primary winding if the squelch signal 87 is used, as illustrated in FIG. 5. From a comparison of the graphs in FIGS. 8A and 8B, it may be appreciated that employing the squelch signal 87 facilitates a reduction in a surge current in the primary winding during a detectable indication, due to the fact that, in this embodiment, the detector 80 responds more quickly to detectable indications on the power channel than does the excitation control circuit 26. It should be appreciated, however, that the energy transfer system of FIG. 5 may effectively regulate power with or without the implementation of the squelch signal 87.

Figure 9A:
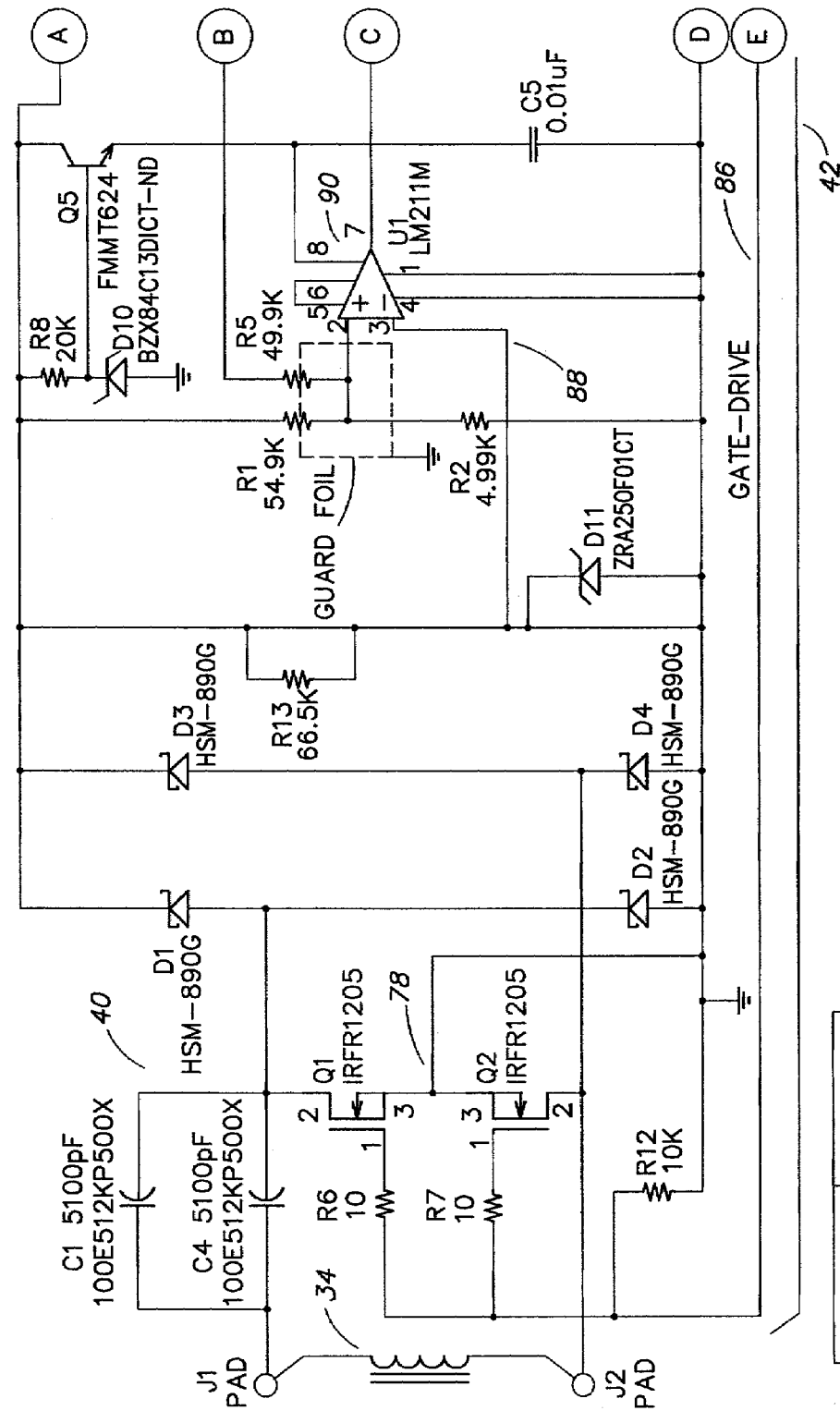
Figure 9B:
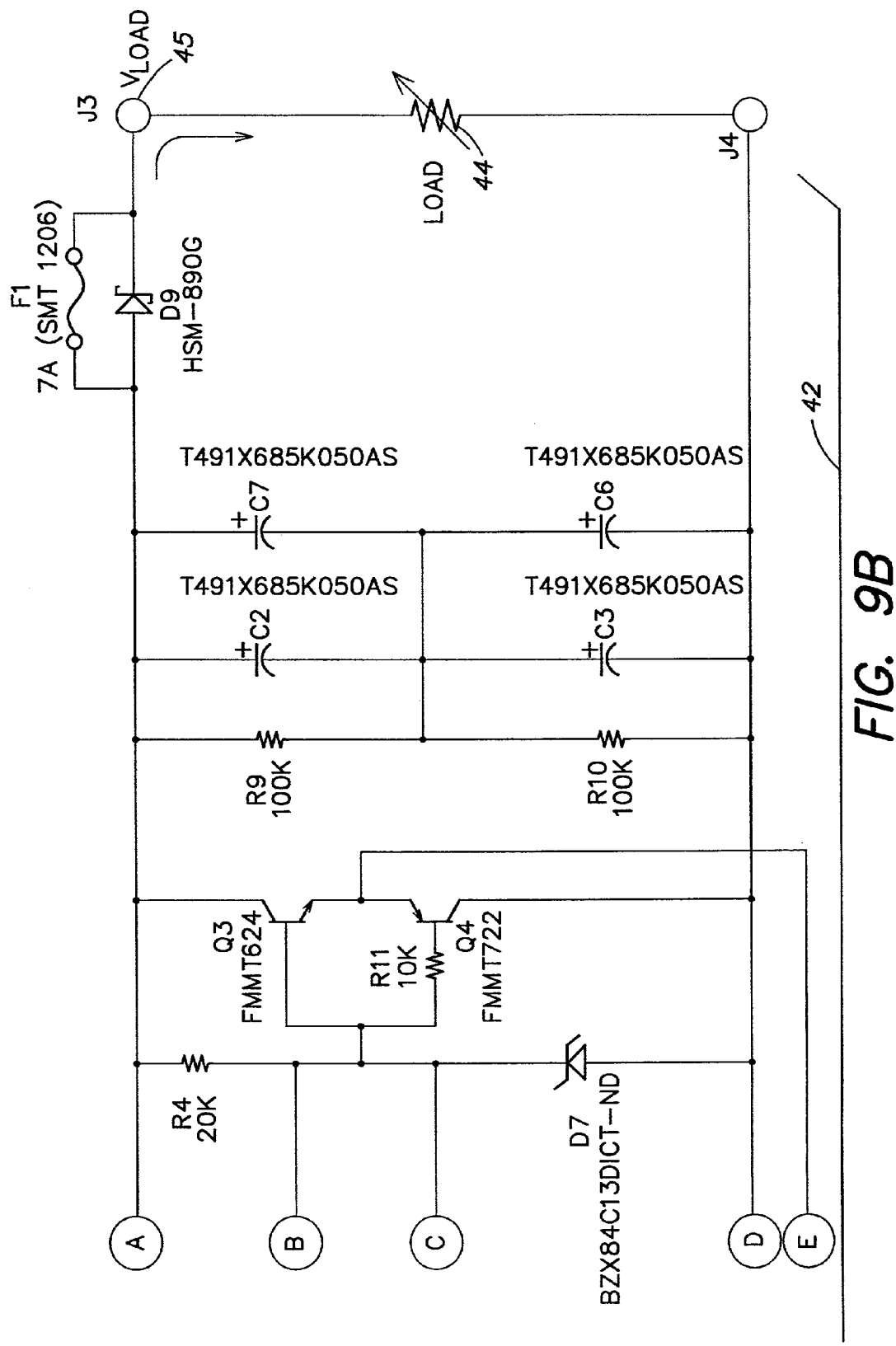
Figure 10A:
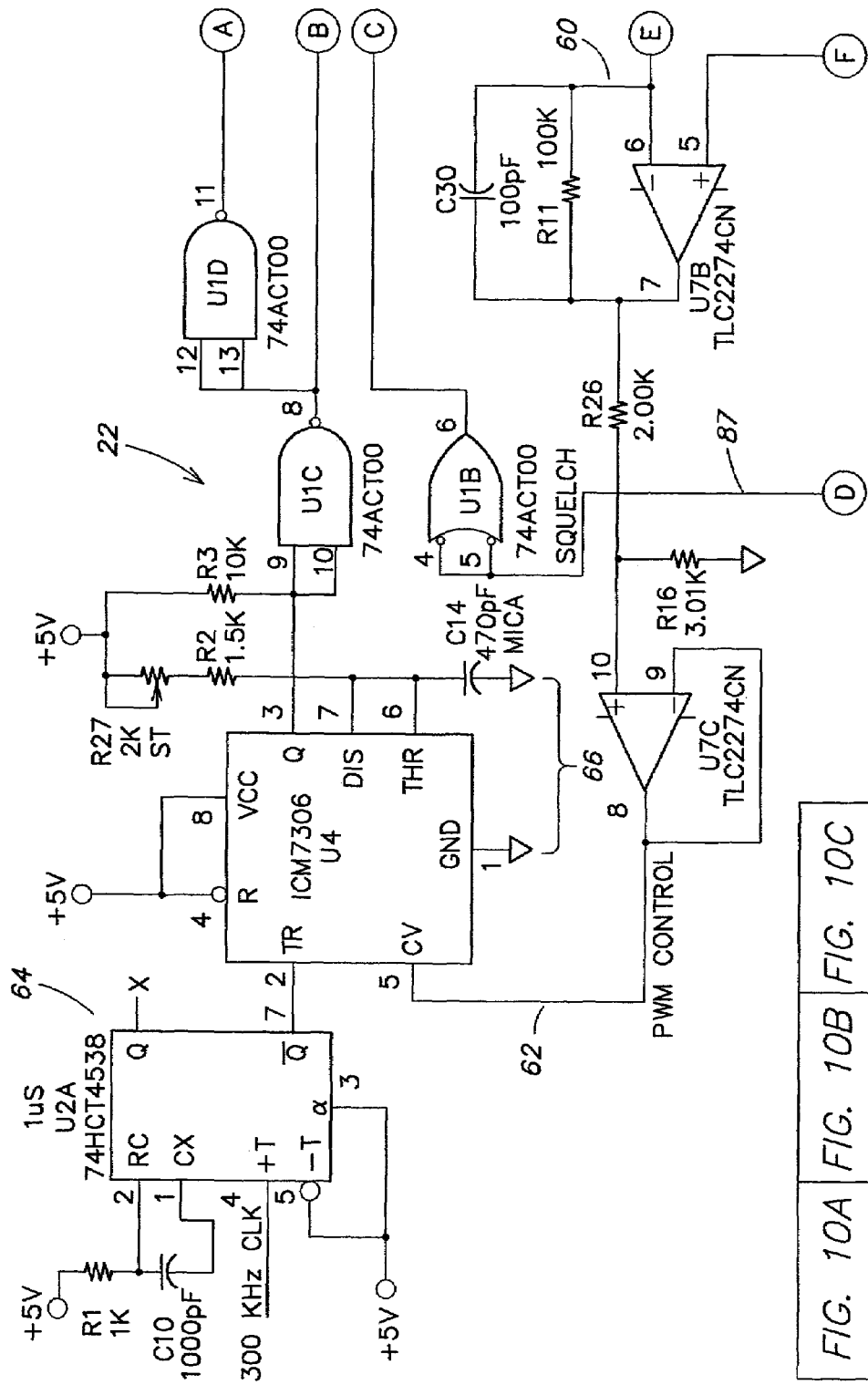
Figure 10B:
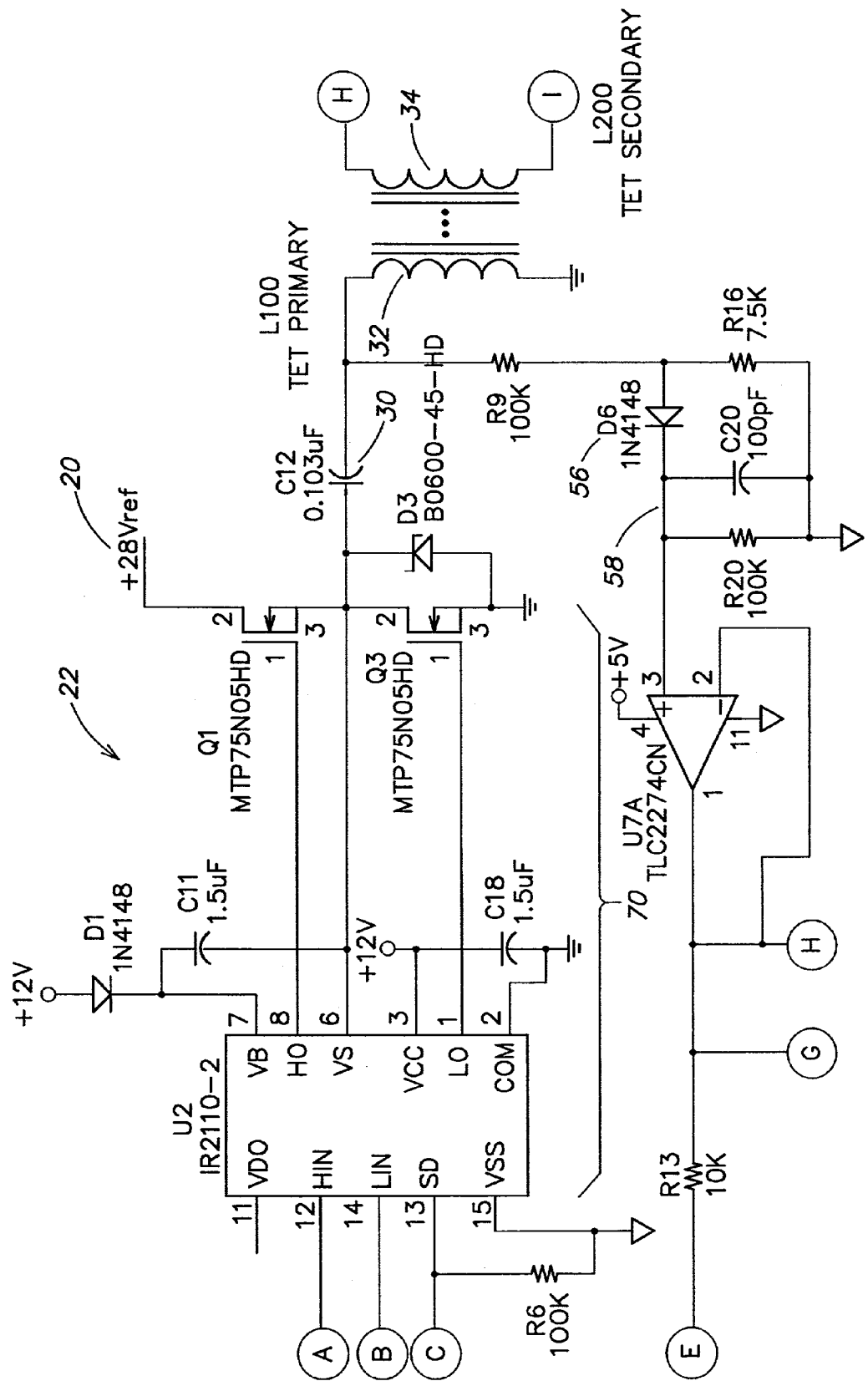
Figure 10C:
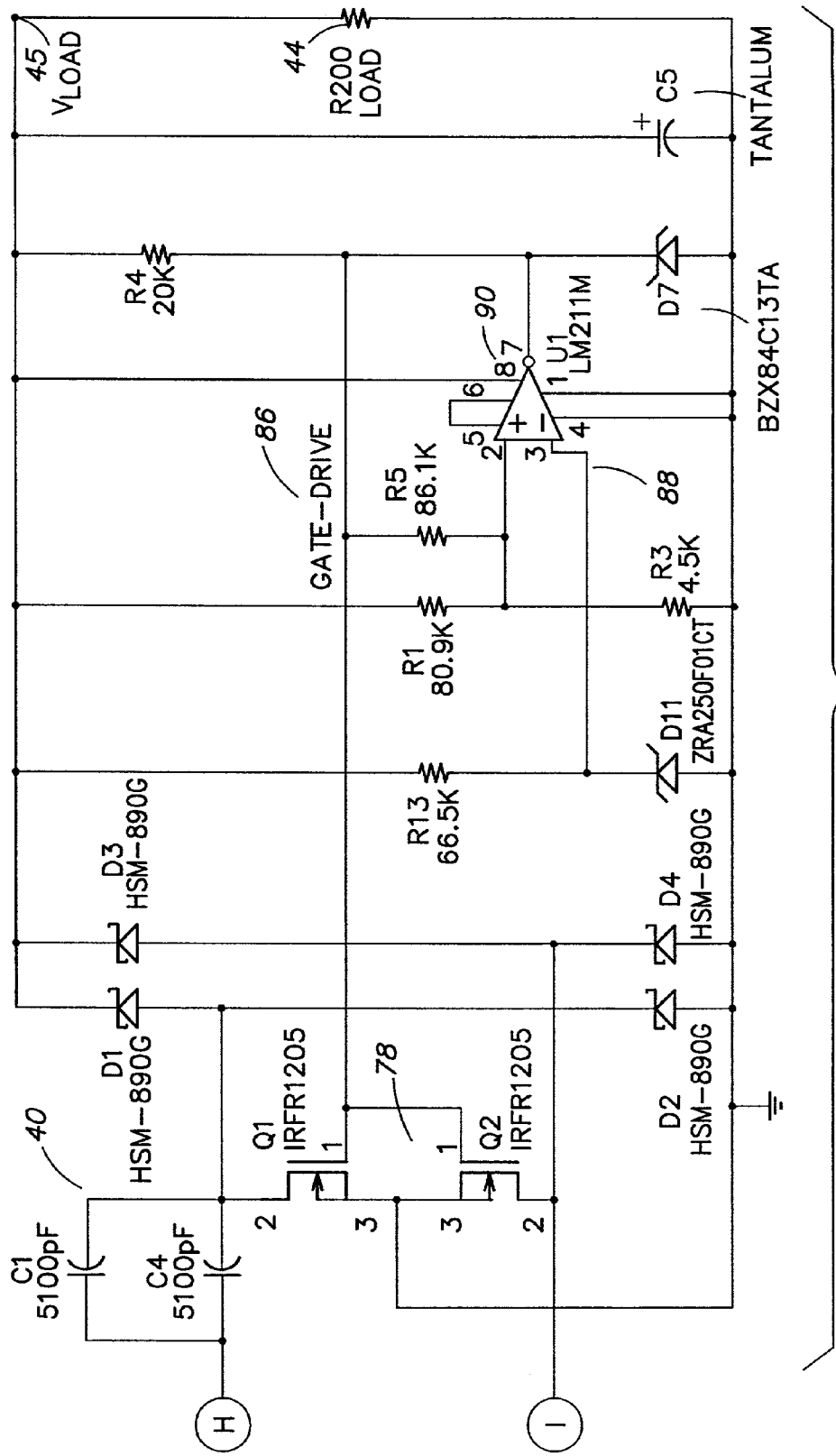
Figure 10D:
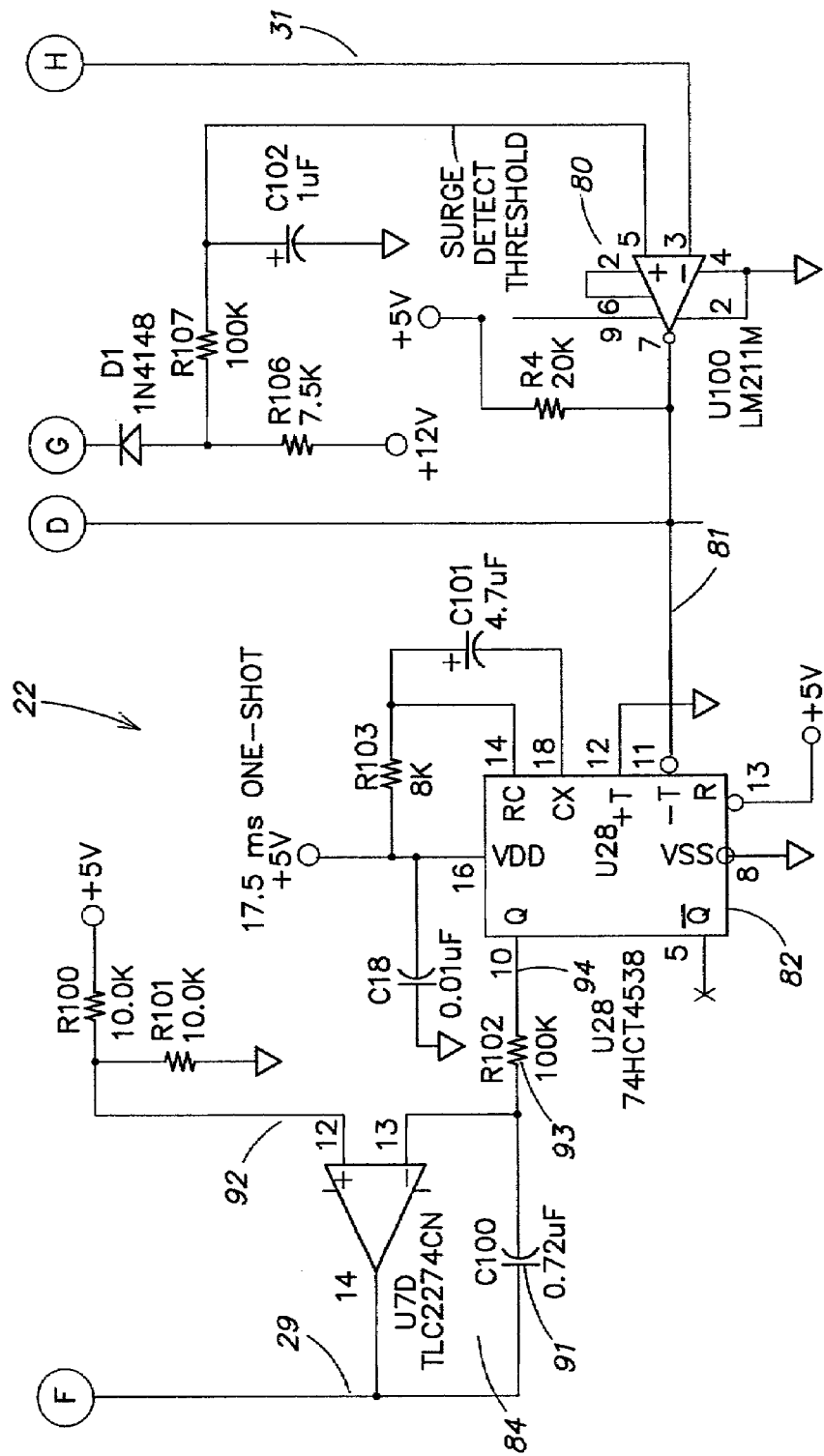
Figure 11A:
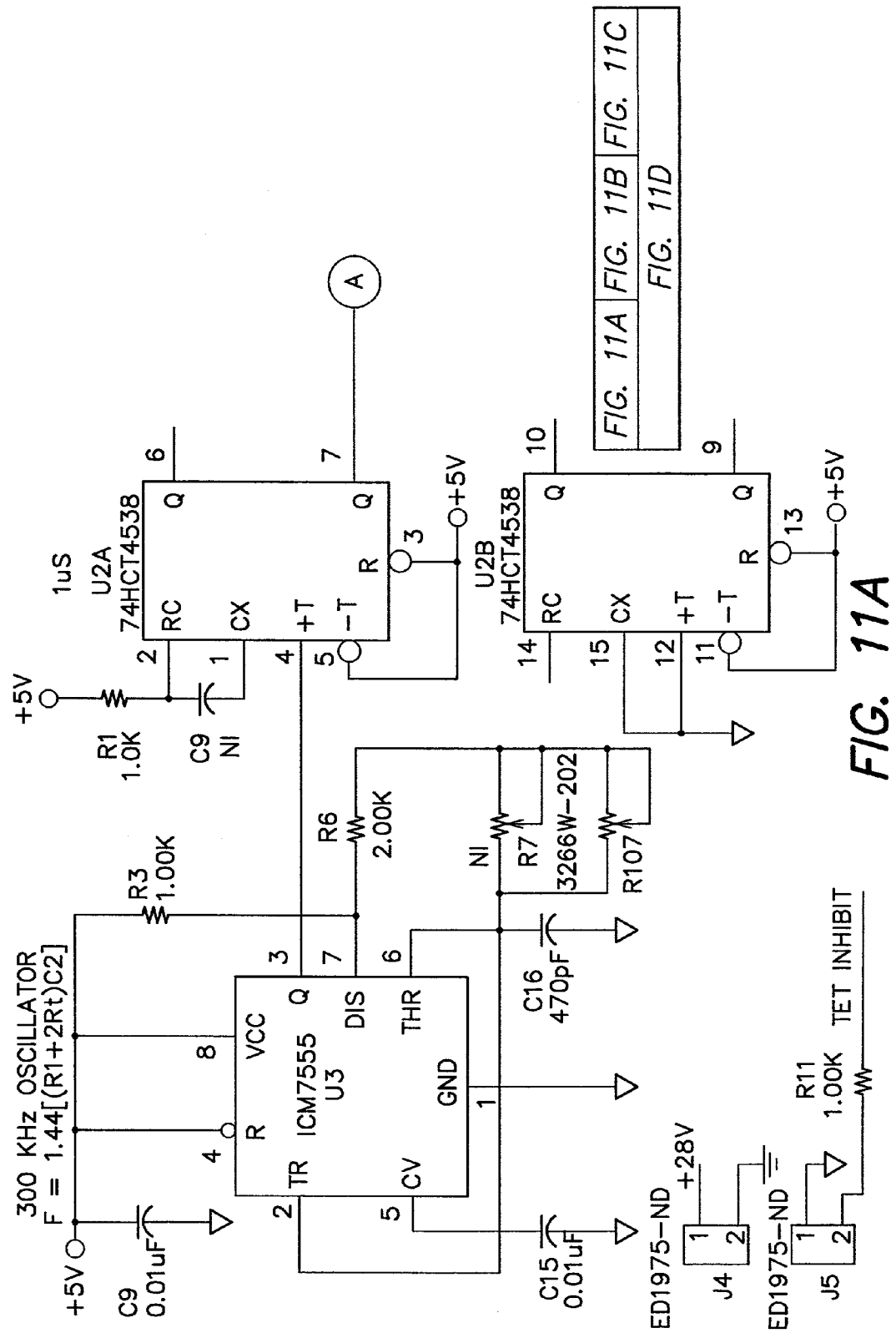
Figure 11B:
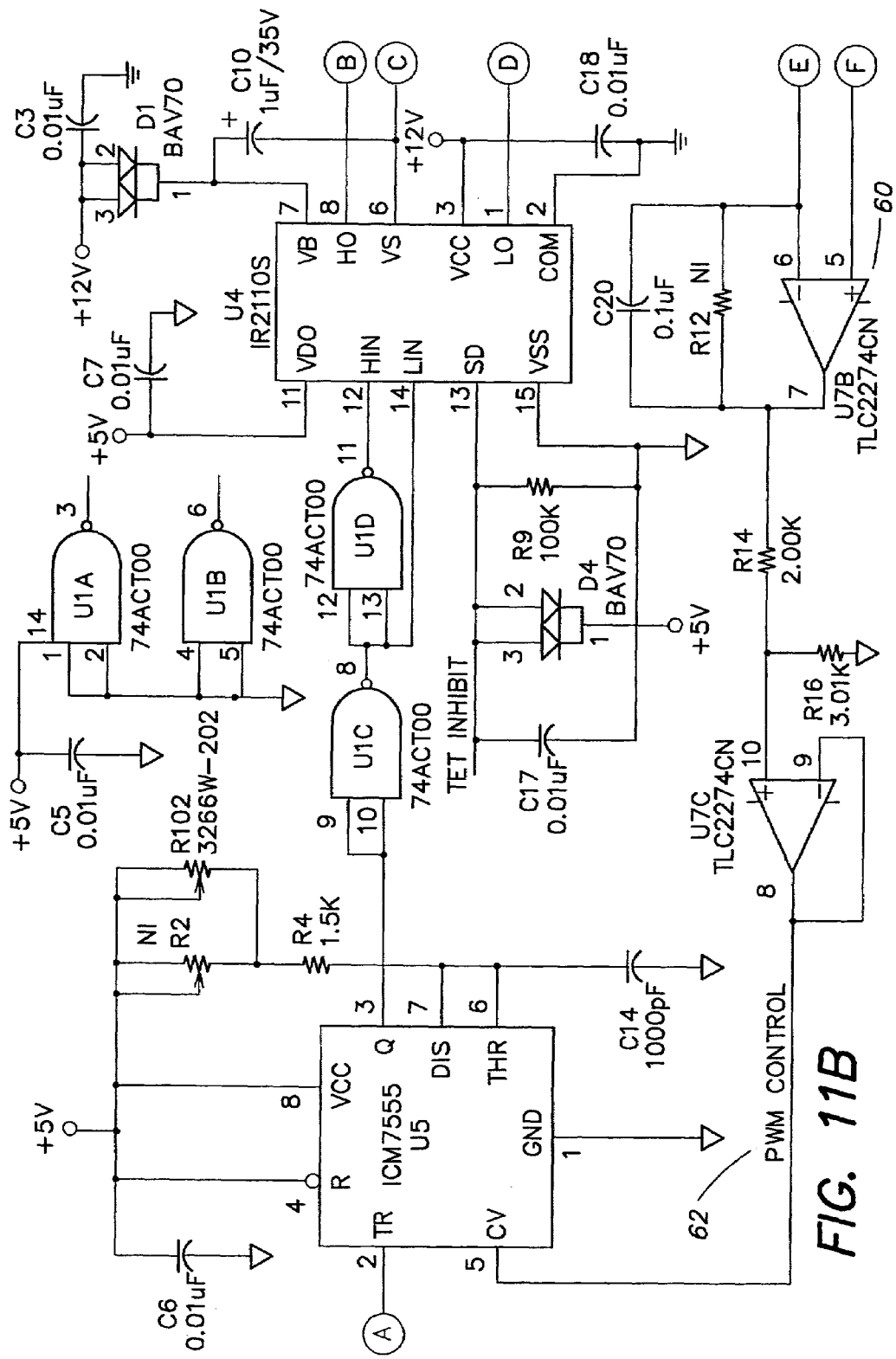
Figure 11C:
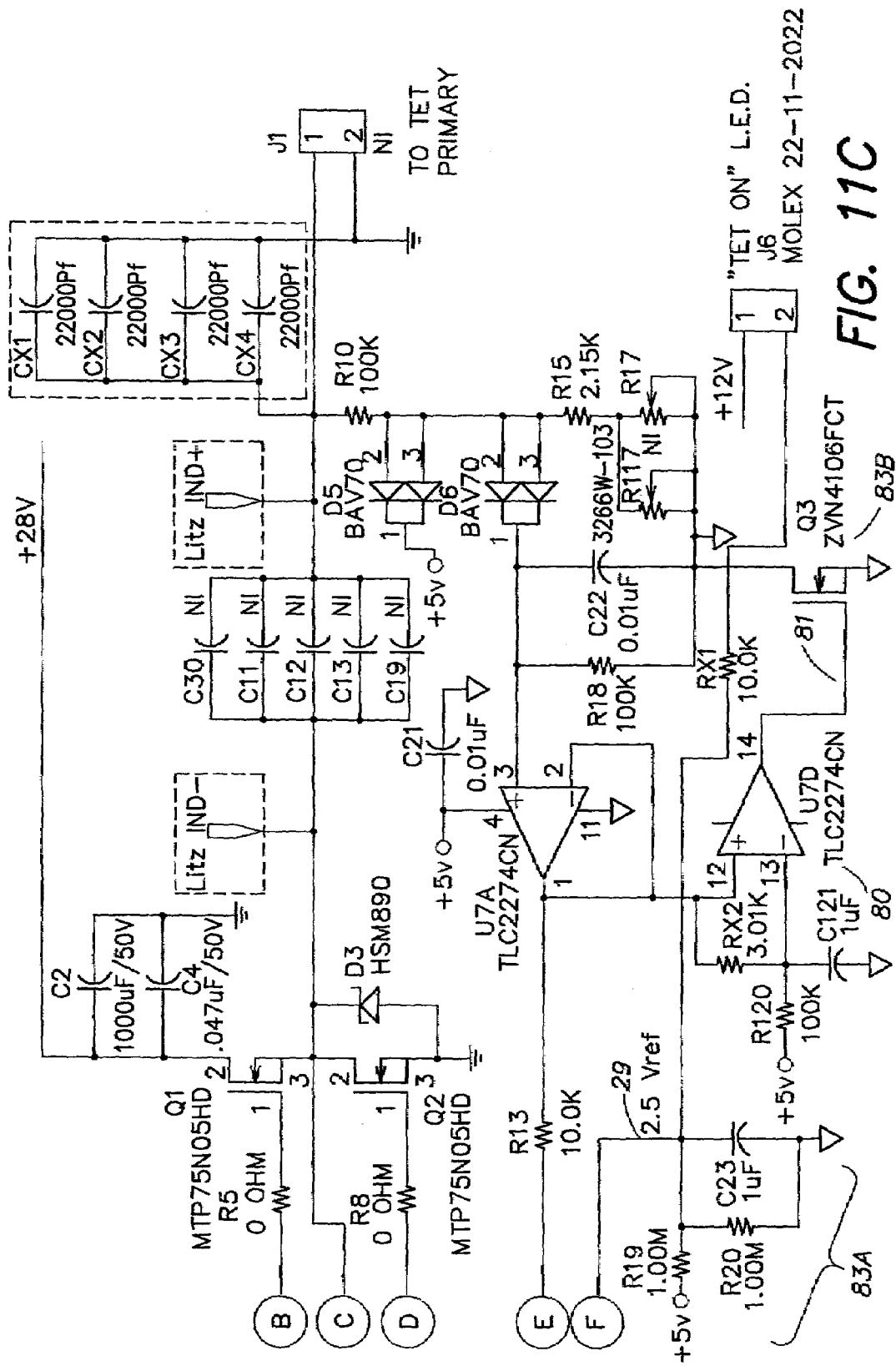
Figure 11D:
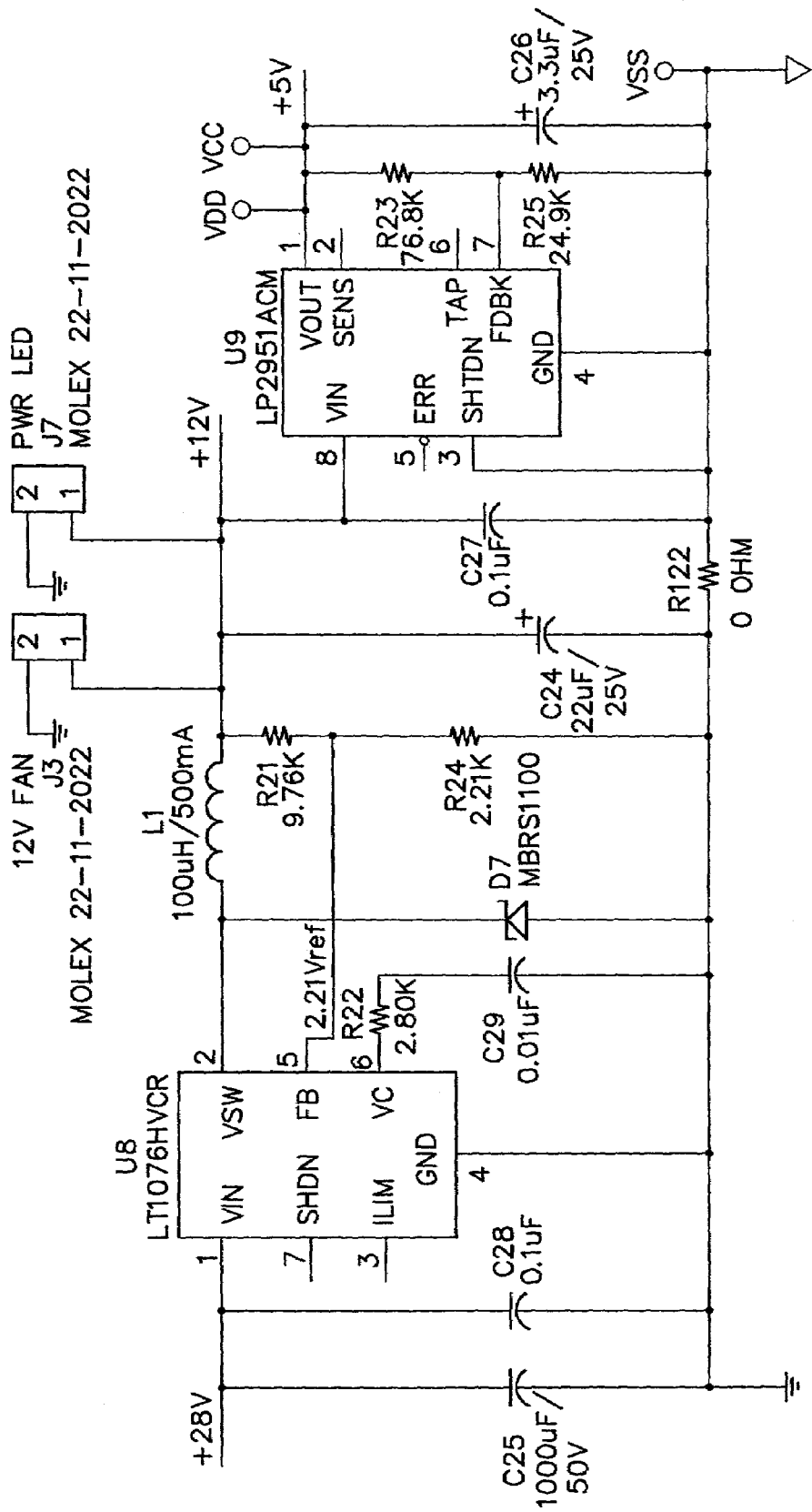

FIG. 9 is a circuit diagram showing one example of an electronic circuit implementation of a secondary side of the energy transfer system shown in FIG. 5, according to one embodiment of the invention. In the exemplary circuit of FIG. 9, a self-inductance of the secondary winding 34 is approximately 30 μH. A mutual inductance between the primary winding 32 and the secondary winding 34 is approximately 0.4 μH. Consequently, since the self-inductance in this example is significantly larger than the mutual inductance of the windings, most of the secondary winding self-inductance appears in series with the load 44. Capacitors C1 and C4, which constitute the secondary capacitor 40 shown in other figures, are selected such that a resonance frequency of the secondary circuitry is approximately 300 kHz, at which frequency the secondary winding has an inductive reactance of approximately 50 ohms. The capacitors C1 and C4 reduce the reactance to a few ohms.

In the secondary circuit 42 shown in the example of FIG. 9, diodes D1–D4 form a fill wave bridge rectifier, and a capacitor network formed by the capacitors C2, C3, C6 and C7 acts to smooth the rectifier output voltage. Resistors R9 and R10 function to balance a DC voltage across the capacitor network. Transistors Q1 and Q2 at the input of the bridge rectifier constitute the surge generator 78, and are turned on to shunt the secondary voltage. Comparator 90 (U1) senses the load voltage 45 through a resistor divider formed by R1, R2, and R5. When a voltage at an output of this divider exceeds the threshold voltage 88 applied to the inverting input of the comparator 90, which in this example is set at approximately 2.5 Volts, the signal 86 goes high to drive the transistors Q1 and Q2. The comparator output that ultimately generates the signal 86 is buffered by transistors Q3 and Q4. Resistors R6 and R7 dampen oscillations that may occur when the gate terminals of transistors Q1 and Q2 are driven in parallel by the signal 86. Zener diode D7 limits the gate voltage of transistors Q3 and Q4 to protect the transistors Q1 and Q4. Resistor R5 provides positive feedback to the comparator 90 which establishes a reset level for the over-voltage detection that is several volts lower than the activation threshold level (i.e., a hysteresis band) to reduce noise sensitivity and prevent high frequency oscillation.

Using the component values shown in the exemplary circuit of FIG. 9 (i.e., R1=54.9 Kohms, R2=4.99 Kohms, and R5=49.9 Kohms), the signal 86 goes high to activate the transistors Q1 and Q2 when the load voltage 45 is approximately 33 Volts, and goes low to deactivate the transistors Q1 and Q2 when the load voltage 45 is approximately 19 Volts. However, it should be appreciated that the invention is not limited to the particular arrangement of components and the particular component values illustrated in FIG. 9, and that other circuit configurations are possible to implement the various functions of the secondary circuit 42 discussed herein, according to various embodiments of the invention. For example, in one embodiment, the various components discussed above in FIG. 9 may be selected such that the signal 86 goes high to activate the transistors Q1 and Q2 when the load voltage 45 is in a range of from approximately 30 Volts to approximately 45 Volts, and such that the signal 86 goes low to deactivate the transistors Q1 and Q2 when the load voltage 45 is in a range of from approximately 20 Volts to approximately 30 Volts.

FIG. 10 is a circuit diagram showing one example of an electronic circuit implementation of both the primary and secondary sides of the energy transfer system shown in FIG. 5, according to one embodiment of the invention. The secondary circuit 42 shown in FIG. 10 is substantially similar to that shown in FIG. 9. Similarly, the primary circuit 22 shown in FIG. 10 is substantially similar to that shown in FIG. 3D, albeit with the addition of components related to the variable reference control circuit 31.

In the exemplary circuit of FIG. 10, comparator U100 of the reference control circuit 31 serves as a portion of the surge detector 80, which receives as an input the rectified and filtered monitored primary amplitude signal and a variable surge detector threshold signal that tracks a short-term average of the monitored primary amplitude signal, with an offset of one diode forward voltage drop to provide some noise immunity. Without the offset to the short-term average voltage used as the reference for the comparator U100, both inputs of the comparator U100 dwell at essentially the same voltage, making it very sensitive to input noise. An output of the comparator U100 provides the detected indication signal 81 as well as the squelch signal 87. The detected indication signal 81 triggers the integrated circuit U28, which serves as the timer 82. The resistive and capacitive components associated with the timer U28 are selected to effect a desired frequency for the variable reference parameter 29. In the particular example shown in FIG. 10, these components are selected such that the timer has a time constant of approximately 17.5 milliseconds, which ultimately results in a frequency of approximately 28 Hz for the timer output signal 94 (and, hence, the variable reference parameter 29). It should be appreciated, however, that the invention is not limited in this respect, as other time constants and resulting frequencies may be suitable in other embodiments of the invention. For example, as discussed above in connection with FIGS. 5 and 7, in one embodiment the frequency of the timer output signal 94 is selected to be in a range of from approximately 5 Hz to approximately 40 Hz.

To generate the variable reference parameter 29, the primary circuit 22 shown in FIG. 10 also includes the integrator output circuit 84. The inverting input of this integrator receives the timer output signal 94. In the exemplary circuit of FIG. 10, the timer output signal 94 switches between 0 Volts and 5 Volts, and the non-inverting input of the integrator is biased at a reference voltage 92 of 2.5 Volts. Under these conditions, the reference parameter 29 is in equilibrium when the timer output signal 94 spends equal time in the high and low states.

As discussed above in connection with FIG. 5, in the circuit of FIG. 10 if the detector 80 detects one or more indications, the timer 82 is triggered to go to a high state for time equal to the time constant of the timer. The timer is retriggerable and remains in the high state if indications continue to be detected. While the timer output signal is in a high state, the reference parameter 29 ramps downward at a rate related to the component values of the capacitor 91 and the resistor 93, thereby decreasing the primary amplitude 46. As the primary amplitude decreases, eventually the secondary circuit 42 stops generating detectable indications, and the detector 80 stops triggering the timer 82. The reference parameter 29 continues ramping down until the timer output signal resets to a low level, after which the reference parameter 29 begins ramping up again (at a rate related to the component values of the capacitor 91 and the resistor 93) until indications generated by the secondary circuit are again detected.

FIG. 11 is a circuit diagram showing another example of an electronic circuit implementation of the primary side of the energy transfer system of FIG. 5, according to one embodiment of the invention. In particular, in the circuit of FIG. 11, an implementation alternative to that shown in FIG. 10 is given for the reference control circuit 31. More specifically, with reference again to FIG. 5, the detector 80, the timer 82, and the output circuit 84 of the reference control circuit 31 are implemented in FIG. 11 using the operational amplifier U7D and several other circuit components associated therewith.

In the circuit of FIG. 11, the non-inverting input of the operational amplifier U7A receives a rectified and filtered monitored primary amplitude signal. The inverting input of operational amplifier U7A receives a low-pass filtered version of this signal (as a result of the resistor RX2 and the capacitor C121), with a small bias added via resistor R120. The output of U7A is received by the surge detector 80 (operational amplifier U7D), which provides the detected indication signal 81.

In FIG. 11, the detected indication signal 81 is used to activate transistor Q3 (labeled with reference character 83B) which, when activated, provides a discharge path for capacitor C23 through resistor RX1. The capacitor C23, together with resistors R19 and R20 (collectively labeled with reference character 83A in FIG. 11) provide the varying reference voltage 29 to the comparator 60 (operational amplifier U7B). Accordingly, the circuit components collectively designated by 83A and 83B in FIG. 11 provide alternative circuit implementations for the timer 82 and the output circuit 84 shown in FIGS. 5 and 10. In particular, detectable indications detected by the surge detector 80 cause the detected indication signal 81 to activate transistor 83B (Q3) for a short time duration, which begins to discharge the capacitor C23, thereby reducing the varying reference voltage 29 at the non-inverting input of U7B. When the transistor 83B is not activated (i.e., in the absence of detected indications), the capacitor C23 is allowed to charge through the resistor R19, and the varying reference voltage 29 increases accordingly. Hence, the varying reference voltage 29 is allowed to increase until a detectable indication is detected, which then activates the transistor 83B, begins to discharge capacitor C23, and decreases the reference voltage 29. It should be appreciated that, in this embodiment, the waveform of the reference voltage 29 is not necessarily a triangular waveform, but rather has an exponential shape representative of a charging and discharging of an RC circuit.

It should be appreciated that the foregoing discussion of the exemplary circuits of FIGS. 9–11 is for purposes of illustration only, and that the invention is not limited to these specific implementations.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. An energy receiving system for receiving power transferred from a power supply located on a first side of a physical boundary and delivering the power to a variable load located on a second side of the physical boundary, the energy receiving system comprising:
- a secondary winding electrically coupled to the variable load to provide power to the variable load based on a magnetic field received by the secondary winding, the secondary winding adapted to be disposed on the second side of the physical boundary and for magnetic coupling with a primary winding disposed on the first side of the physical boundary to form a power channel between the windings through which the magnetic field is received by the secondary winding;
- a secondary control circuit electrically coupled to the secondary winding to provide a detectable indication on the power channel that indicates at least one of changes in the variable load and changes in the relative position of the primary winding and the secondary winding, wherein the detectable indication includes at least one surge on the power channel.

2. The system of claim 1, wherein the secondary control circuit provides the detectable indication on the power channel to indicate a characteristic of the variable load compared to a predetermined threshold for that characteristic.

3. The system of claim 2, wherein the secondary control circuit provides the detectable indication on the power channel to indicate when a load voltage across the variable load one of exceeds and drops below a predetermined threshold load voltage.

4. The system of claim 3, wherein the secondary control circuit includes a comparator electrically coupled to the variable load to compare the load voltage to a predetermined threshold load voltage.

5. The system of claim 1, wherein the secondary control circuit includes a surge generator to generate the at least one surge.

6. The system of claim 5, wherein the secondary control circuit provides the at least one surge on the power channel to indicate a characteristic of the variable load compared to a predetermined threshold for that characteristic.

7. The system of claim 6, wherein the secondary control circuit provides the at least one surge on the power channel to indicate when a load voltage across the variable load one of exceeds and drops below a predetermined threshold load voltage.

8. The system of claim 7, wherein:
- the secondary control circuit includes a comparator electrically coupled to the variable load to compare the load voltage to a predetermined threshold load voltage;
- the comparator is electrically coupled to the surge generator; and
- the secondary control circuit provides the at least one surge on the power channel based on the comparison.

9. The system of claim 8, wherein the surge generator includes a shunt circuit that generates a surge in a current in the secondary winding when an input signal to the shunt circuit reaches a shunt activation level, the comparator providing the input signal having the shunt activation level when the load voltage one of exceeds and drops below the predetermined threshold load voltage.

10. The system of claim 9, wherein:
- the second side of the energy receiving system further includes at least one capacitor coupled to the secondary winding to form a secondary resonant circuit; and
- the shunt circuit generates the surge in the current in the secondary winding by creating a short circuit across the secondary resonant circuit.

11. The system of claim 1, wherein the physical boundary is a patient's skin and the energy receiving system is adapted to be implanted within a patient.

12. In an energy transfer system for transferring power from a power supply located on a first side of a physical boundary to a variable load located on a second side of the physical boundary, the system having a primary winding on the first side for generating a magnetic field based on input power provided by the power supply, the magnetic field permeating the physical boundary for magnetically coupling the primary winding to a secondary winding on the second side, thereby forming a power channel between the windings through which at least a portion of the magnetic field is received by the secondary winding to provide power to the variable load based on the received magnetic field, a system for the second side comprising:
- a secondary winding electrically coupled to the variable load;
- a secondary control circuit electrically coupled to the secondary winding to provide a detectable indication on the power channel that indicates a characteristic of the variable load compared to a predetermined threshold for that characteristic, wherein the detectable indication includes at least one surge on the power channel.

13. The system of claim 12, wherein the secondary control circuit provides the detectable indication on the power channel to indicate when a load voltage across the variable load one of exceeds and drops below a predetermined threshold load voltage.

14. The system of claim 13, wherein the secondary control circuit includes a comparator electrically coupled to the variable load to compare the load voltage to a predetermined threshold load voltage.

15. The system of claim 12, wherein the secondary control circuit includes a surge generator to generate the at least one surge.

16. The system of claim 15, wherein the secondary control circuit provides the at least one surge on the power channel to indicate a characteristic of the variable load compared to a predetermined threshold for that characteristic.

17. The system of claim 16, wherein the secondary control circuit provides the at least one surge on the power channel to indicate when a load voltage across the variable load one of exceeds and drops below a predetermined threshold load voltage.

18. The system of claim 17, wherein:
- the secondary control circuit includes a comparator electrically coupled to the variable load to compare the load voltage to a predetermined threshold load voltage;
- the comparator is electrically coupled to the surge generator; and
- the secondary control circuit provides the at least one surge on the power channel based on the comparison.

19. The system of claim 18, wherein the surge generator includes a shunt circuit that generates a surge in a current in the secondary winding when an input signal to the shunt circuit reaches a shunt activation level, the comparator providing the input signal having the shunt activation level when the load voltage one of exceeds and drops below the predetermined threshold load voltage.

20. The system of claim 19, wherein:
- the second side of the energy receiving system further includes at least one capacitor coupled to the secondary winding to form a secondary resonant circuit; and
- the shunt circuit generates the surge in the current in the secondary winding by creating a short circuit across the secondary resonant circuit.

21. The system of claim 12, wherein the physical boundary is a patient's skin and the system for the secondary side is adapted to be implanted within a patient.

22. In an energy transfer system for transferring power from a power supply located on a first side of a physical boundary to a variable load located on a second side of the physical boundary, the energy receiving system having a primary winding disposed on the first side and electrically coupled to the power supply to generate a magnetic field based on input power provided by the power supply, the magnetic field permeating the physical boundary for magnetically coupling a secondary winding disposed on the second side to the primary winding, thereby forming a power channel between the windings through which at least a portion of the magnetic field is received by the secondary winding, the secondary winding electrically coupled to the variable load to provide power to the variable load based on the received magnetic field, a method of providing power to the variable load comprising:
providing power to the variable load based on a magnetic field received by the secondary winding from the primary winding;
comparing a characteristic of the variable load to a predetermined threshold for that characteristic on the second side of the physical boundary; and
generating a detectable indication on the power channel based on the comparison for transmission across the physical boundary, wherein the generating a detectable indication on the power channel includes generating at least one surge on the power channel based on the comparison.

23. The method of claim 22, wherein the comparing is of a load voltage across the variable load to a predetermined threshold load voltage.

24. The method of claim 23, wherein the comparing indicates when the load voltage one of exceeds and drops below the predetermined threshold load voltage.

25. The method of claim 22, wherein the generating at least one surge on the power channel based on the comparison includes generating a surge in a current in the secondary winding.

26. The method of claim 25, wherein the generating the surge in the current in the secondary winding includes diverting power away from the variable load and into the secondary winding when the comparison reaches an activation level.

27. The method of claim 26, wherein the diverting power away from the variable load and into the secondary winding includes generating a short circuit across the secondary winding when the comparison reaches the activation level.

28. The method of claim 27, wherein the activation level is when the comparison indicates that a load voltage across the variable load one of exceeds and drops below a predetermined threshold load voltage.

29. The system of claim 22, wherein the physical boundary is a patient's skin and the step of providing power includes transferring power across the patient's skin.

* * * * *

UNITED STATES PATENT AND TRADEMARK OFFICE
CERTIFICATE OF CORRECTION

PATENT NO.          : 7,155,291 B2                              Page 1 of 1
APPLICATION NO.  : 10/136089
DATED                  : December 26, 2006
INVENTOR(S)         : Farhad Zarinetchi et al.

It is certified that error appears in the above-identified patent and that said Letters Patent is hereby corrected as shown below:

In the Specification:

At column 5, line 47, change "to-the" to --to the--.

At column 7, line 35, change "unction" to --function--.

At column 12, line 19, change "RIO" to --R10--.

At column 18, line 27, change "fill" to --full--.

Signed and Sealed this

Sixth Day of March, 2007

JON W. DUDAS
*Director of the United States Patent and Trademark Office*